United States Patent
Timmermann et al.

(10) Patent No.: US 8,598,339 B2
(45) Date of Patent: Dec. 3, 2013

(54) **WITHANOLIDE ISOLATED FROM *PHYSALIS LONGIFOLIA* AND ANALOGS AND METHODS OF USE THEREOF**

(75) Inventors: Barbara N. Timmermann, Lawrence, KS (US); Jeffrey Aube, Lawrence, KS (US); Huaping Zhang, Hanchuan (CN); Rao Gollapudi, Goa (IN); Mark S. Cohen, Overland Park, KS (US); Abbas Samadi, Prairie Village, KS (US); Hashim Fakhsuddin-Motiwala, Mumbai (IN)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/363,476

(22) Filed: Feb. 1, 2012

(65) Prior Publication Data

US 2012/0196815 A1 Aug. 2, 2012

Related U.S. Application Data

(60) Provisional application No. 61/438,367, filed on Feb. 1, 2011.

(51) Int. Cl.
*C07J 71/00* (2006.01)

(52) U.S. Cl.
USPC .......................................................... 540/80

(58) Field of Classification Search
USPC .......................................................... 540/80
See application file for complete search history.

(56) References Cited

U.S. PATENT DOCUMENTS

| 7,282,593 | B2 | 10/2007 | Nair et al. ...................... 548/454 |
| 2009/0088412 | A1 | 4/2009 | Wu et al. ........................ 514/175 |

FOREIGN PATENT DOCUMENTS

| WO | WO 2010/030395 A2 | 3/2010 |
| WO | WO 2010/053655 A2 | 5/2010 |

OTHER PUBLICATIONS

Zhang et al. J. Nat. Prod. 2011, 74, 2532-2544.*
Anbalagan, K. and Sadique, J. "Influence of an Indian Medicine (Ashwagandha) on Acute-phase Reactants in Inflammation" Indian Journal of Experimental Biology 1981 19(3):245-249.
Bargagna-Mohan et al. "The Tumor Inhibitor and Antiangiogenic Agent Withaferin A Targets the Intermediate Filament Protein Vimentin" Chemistry & Biology 2007 14(6):623-634.
Dhuley, J. N. "Adaptogenic and Cardioprotective Action of Ashwagandha in Rats and Frogs" Journal of Ethnopharmacology 2000 70:57-63.
Dhuley, J. N. "Effect of Ashwagandha on Lipid Peroxidation in Stress-induced Animals" Journal of Ethnopharmacology 1998 60:173-178.
Dhuley, J. N. "Effect of Some Indian Herbs on Macrophage Functions in Ochratoxin A Treated Mice" Journal of Ethnopharmacology 1997 58:15-20.
Falsey et al. "Actin Microfilament Aggregation Induced by Withaferin A Is Mediated by Annexin II" Nature Chemical Biology 2006 2(1):33-38.
Jayaprakasam et al. "Growth Inhibition of Human Tumor Cell Lines by Withanolides from *Withania somnifera* Leaves" Life Sciences 2003 74:125-132.
Kaileh et al. "Withaferin A Strongly Elicits IκB Kinase β Hyperphosphorylation Concomitant with Potent Inhibition of its Kinase Activity" The Journal of Biological Chemistry 2007 282(7):4253-4264.
Lavie et al. "Constituents of *Withania somnifera* Dun. III. The Side Chain of Withaferin A" The Journal of Organic Chemistry 1965 30(6):1774-1778.
Ray, A. B. and Gupta, M. "Withasteroids, a Growing Group of Naturally Occurring Steroidal Lactones" Progress in the Chemistry of Organic Natural Products 1994 63:1-106.
Sen et al. "Apoptosis Is Induced in Leishmanial Cells by a Novel Protein Kinase Inhibitor Withaferin A and Is Facilitated by Apoptotic Topoisomerase I-DNA Complex" Cell Death and Differentiation 2007 14:358-367.
Srinivasan et al. "Par-4-dependent Apoptosis by the Dietary Compound Withaferin A in Prostate Cancer Cells" Cancer Research 2007 67:246-253.
Yang et al. "The Tumor Proteasome Is a Primary Target for the Natural Anticancer Compound Withaferin A Isolated from 'Indian Winder Cherry'" Molecular Pharmacology 2007 71(2):426-437.
Ziauddin et al. "Studies on the Immunomodulatory Effects of Ashwagandha" Journal of Ethnopharmacology 1996 50:69-76.

* cited by examiner

*Primary Examiner* — Nizal Chandrakumar
(74) *Attorney, Agent, or Firm* — Licata & Tyrrell P.C.

(57) ABSTRACT

The present invention features novel withanolides, as well as analogs and salts thereof, for use in the treatment of proliferative disease, cardiovascular disease, neurodegenerative disease and inflammatory disease.

3 Claims, No Drawings

WITHANOLIDE ISOLATED FROM *PHYSALIS LONGIFOLIA* AND ANALOGS AND METHODS OF USE THEREOF

This patent application claims the benefit of priority from U.S. Provisional Application Ser. No. 61/438,367 filed Feb. 1, 2011, the contents of which are incorporated herein by reference in their entirety.

BACKGROUND OF THE INVENTION

Plant-based medicines or drugs are of ancient origin and their use is known in cultures throughout the world. A common concern with herbal medicine is that herbs are slow acting in treating an ailment. Therefore, a movement to identify individual active ingredients in beneficial plants developed in the 18th century, leading into a transitional period from the use of plant-based products to the use of pharmaceutical drugs such as extracts and purified chemicals, sometimes referred to as allopathic drugs, which act comparatively quickly.

Many active herbal compounds have been extracted and chemically synthesized for use in the modern allopathic medical practice. For example, Indian snake root, also known as *Rauwolfia serpentina*, has been used in Indian ayurvedic medicine for centuries to cure anxiety, headaches, and high blood pressure. In 1947, the alkaloid, reserpine, was extracted from snake root and used in the treatment of hypertension.

Similarly, the roots of the medicinal plant *Withania somnifera* (L.) Dunal have been used in the Ayurvedic tradition of India as it possesses a variety of activities including anti-inflammatory (Anbalagan, et al. (1981) *Indian J. Exp. Biol.* 19:245-249), immunomodulatory (Ziauddin, et al. (1996) *J. Ethnopharmacol.* 50:69-76; Dhuley, et al. (1997) *J. Ethnopharmacol.* 58:15-20), cardioprotective (Dhuley, et al. (2000) *J. Ethnopharmacol.* 70:57-63), antioxidant (Dhuley, et al. (1998) *J. Ethnopharmacol.* 60:173-178), and antiproliferative (Jayaprakasam, et al. (2003) *Life Sci.* 74:125-132) activities. The primary bioactive constitutents of *W. somnifera* are known as withanolides. These compounds are structurally diverse steroidal compounds with an ergosterol skeleton in which C-22 and C-26 are oxidized to form a δ-lactone (Ray, et al. (1994) *Prog. Chem. Org. Nat. Prod.* 63:1-106). Withaferin A, the first member of this group, was isolated from *W. somnifera* in 1965 (Lavie, et al. (1965) *J. Org. Chem.* 30:1774-1776).

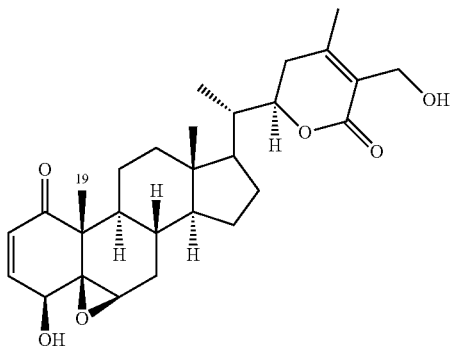

Withaferin A

Withaferin A and related withanolides has been proposed to inhibit the actions of many targets including the actin bundling protein annexin II (Falsey, et al. (2006) *Nat. Chem. Biol.* 2:33-38), the 20S proteasome (Yang, et al. (2007) *Mol. Pharmacol.* 71:426-437), the intermediate filament protein vimentin (Bargagna-Mohan, et al. (2007) *Chem. Biol.* 14:623-634), the transcription factor NFκB (Srinivasan, et al. (2007) *Cancer Res.* 67:246-253), protein kinase C (Sen, et al. (2007) *Cell Death Differ.* 14:358-367), and the Par-4-dependent apoptosis pathway (Kaileh, et al. (2007) *J. Biol. Chem.* 282:4253-4264). Given its various activities, various withaferin analogs have been described. See US 2009/0088412; U.S. Pat. No. 7,282,593; WO 2010/030395; and WO 2010/053655.

An increasing number of people are gaining awareness of the advantages of natural products together with a concern over the disadvantages of modern purified drugs. Consequently, there has been an increasing public interest in the identification of new natural products.

*Physalis longifolia* is a plant native to Kansas. *Physalis longifolia*, or longleaf groundcherry, occurs throughout the continental United States and into southern Canada. It has a characteristic husked fruit, like tomatillos and the cultivated garden plant known as Chinese lantern, which is in the same genus. These plants are part of the nightshade family, Solanaceae, which includes tomatoes, potatoes, and tobacco. *Physalis longifolia* fruit was used as a food source by southwestern Native American tribes, including the Zuni and other Puebloan people. It has now been found that this plant contains a withanolide similar in structure to withaferin A.

SUMMARY OF THE INVENTION

The present invention feature a compound of Formula A compound of Formula I, II, III, IV, V, VI, VII, VIII, IX, X, XI, XII, XIII, XIV, XV, XVI or XVII, or a pharmaceutically acceptable salt or prodrug thereof.

A pharmaceutical composition containing a compound of the invention is also provided as are methods of using compounds of the invention for treating a proliferative disease such as cancer; treating a cardiovascular disease such as hypertension or ischemia; treating a neurodegenerative disease such as Parkinson's disease, Huntington's disease, or Alzheimer's disease; and treating an inflammatory disease such as arthritis or asthma.

Further methods of the invention include methods for activating a heat shock response in a cell; disrupting cytoskeletal organization in a cell; inducing F-actin aggregation in a cell; and inhibiting neuronal death or deterioration.

A method for isolating a withanolide from *Physalis longifolia* is also a feature of this invention.

DETAILED DESCRIPTION OF THE INVENTION

The present invention provides a novel withanolide isolated from the aerial parts of *Physalis longifolia* (Family: Solanaceae). This compound, designated herein as X001, has a typical ergosterol skeleton, but includes an unexpected modification to C-19. The instant compound, and analogs thereof, exhibit anti-tumor activity and therefore find application in the treatment of proliferative diseases such as cancer, benign neoplasms, and diseases involving neoangiogenesis. Moreover, given their structure, these compounds are also of use in the treatment of disorders involving neoangiogenesis, autoimmune diseases, inflammatory diseases, cardiovascular diseases, neurodegenerative diseases, and protein aggregation disorders.

Compounds of the present invention include withanolides having the structure of Formula (I):

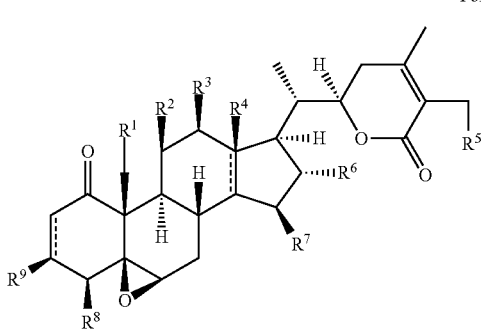

Formula I or a pharmaceutically acceptable salt or prodrug thereof, wherein $R^1$ and $R^8$ are each $-OR^B$, wherein each occurrence of $R^B$ is independently hydrogen, $-SO_3H$, $-PO_3H_2$, $-C(=O)R^C$, $-C(=O)-CH(R^C)-N(R^C)_2$, $-C(=O)N(R^C)_2$, $-CO_2R^C$, $-SOR^C$, $-SO_2R^C$, or $-C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^2$, $R^3$, $R^5$, $R^7$ and $R^9$ are each independently hydrogen or $-OR^D$, where each occurrence of $R^D$ is independently hydrogen, $-SO_3H$, $-PO_3H_2$, $-C(=O)R^C$, $-C(=O)N(R^C)_2$, $-CO_2R^C$, $-SOR^C$, $-SO_2R^C$ or $-C(R^C)_3$;

$R^4$ is hydrogen or an alkyl group;

$R^6$ is hydrogen or $-OH$; and

===== denotes a single or double bond.

In some embodiments, $R^1$ of Formula I is hydroxyl. In other embodiment, $R^1$ of Formula I is alkoxy. In particular embodiments, $R^1$ of Formula I is acetate.

In certain embodiments, $R^2$ of Formula I is hydrogen. In other embodiments, $R^2$ of Formula I is hydroxyl.

In some embodiments, $R^3$ of Formula I is hydrogen. In certain other embodiments, $R^3$ of Formula I is hydroxyl. In certain embodiments, $R^3$ of Formula I is alkoxy. In certain embodiments, $R^3$ of Formula I is phosphate. In certain embodiments, $R^3$ of Formula I is sulfate. In certain other embodiments, $R^3$ of Formula I is acetate.

In certain embodiments, $R^4$ of Formula I is hydrogen. In other embodiments, $R^4$ of Formula I is $-CH_3$.

In certain embodiments, $R^5$ of Formula I is hydrogen. In certain other embodiments, $R^5$ of Formula I is hydroxyl. In certain embodiments, $R^5$ of Formula I is alkoxy. In certain embodiments, $R^5$ of Formula I is phosphate. In certain embodiments, $R^5$ of Formula I is sulfate. In certain other embodiments, $R^5$ of Formula I is acetate. In other embodiments, $R^5$ of Formula I is a monosaccharide (e.g., glucopyranose). In still other embodiments, $R^5$ of Formula I is a disaccharide (e.g., lactose).

In some embodiments, $R^6$ of Formula I is hydrogen. In other embodiments, $R^6$ of Formula I is hydroxyl.

In one embodiment $R^7$ of Formula I is hydrogen. In other embodiments, $R^7$ of Formula I is hydroxyl. In certain embodiments, $R^7$ of Formula I is alkoxy. In certain embodiments, $R^7$ of Formula I is phosphate. In certain embodiments, $R^7$ of Formula I is sulfate. In certain other embodiments, $R^7$ of Formula I is acetate.

In some embodiments, $R^8$ of Formula I is hydrogen. In other embodiments, $R^8$ of Formula I is hydroxyl. In certain embodiments, $R^8$ of Formula I is alkoxy. In certain embodiments, $R^8$ of Formula I is phosphate. In certain embodiments, $R^8$ of Formula I is sulfate. In certain other embodiments, $R^8$ of Formula I is acetate.

In one embodiment $R^9$ of Formula I is hydrogen. In another embodiment, $R^9$ of Formula I is hydroxyl. In certain embodiments, $R^9$ of Formula I is sulfate. In other embodiments, $R^9$ of Formula I is a monosaccharide (e.g., glucopyranose). In certain embodiments, $R^9$ of Formula I is $-OCH_3$.

In certain embodiments, at least one of $R^1$, $R^5$ or $R^8$ of Formula I is acetate. In other embodiments, at least two of $R^1$, $R^5$ or $R^8$ of Formula I are acetate. In particular embodiments, each of $R^1$, $R^5$ and $R^8$ of Formula I is acetate.

In one embodiment, the compound of Formula I is:

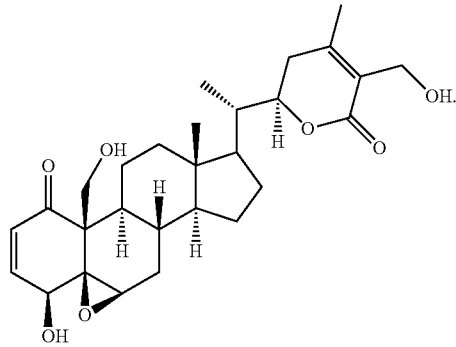

In another embodiment, the compound of Formula I is:

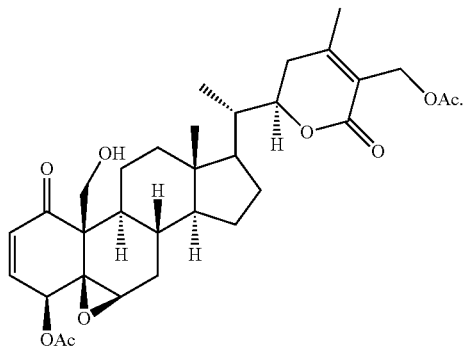

In a further embodiment, the compound of Formula I is:

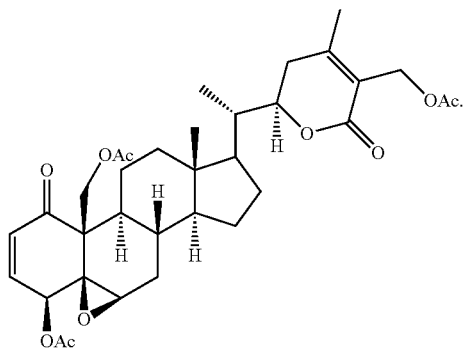

In certain embodiments, the invention provides a compound of Formula II:

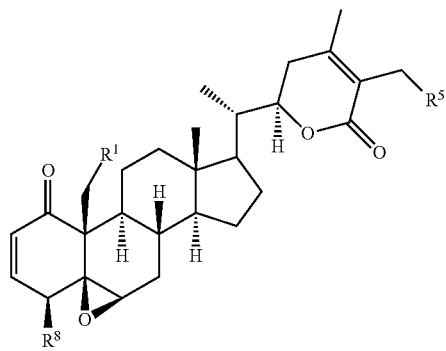

Formula II or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)N(R^C)_2$, —$CO_2R^C$, —$SOR^C$, —$SO_2R^C$, or —$C(R^C)$ wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, or heteroarylthio group; and $R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$.

In some embodiments, $R^1$ of Formula II is hydroxyl. In other embodiment, $R^1$ of Formula II is alkoxy. In particular embodiments, $R^1$ of Formula II is acetate.

In certain embodiments, $R^5$ of Formula II is hydrogen. In certain other embodiments, $R^5$ of Formula II is hydroxyl. In certain embodiments, $R^5$ of Formula II is alkoxy. In certain embodiments, $R^5$ of Formula II is phosphate. In certain embodiments, $R^5$ of Formula II is sulfate. In certain other embodiments, $R^5$ of Formula II is acetate. In other embodiments, $R^5$ of Formula II is a monosaccharide (e.g., glucopyranose). In still other embodiments, $R^5$ of Formula II is a disaccharide (e.g., lactose).

In some embodiments, $R^8$ of Formula II is hydrogen. In other embodiments, $R^8$ of Formula II is hydroxyl. In certain embodiments, $R^8$ of Formula II is alkoxy. In certain embodiments, $R^8$ of Formula II is phosphate. In certain embodiments, $R^8$ of Formula II is sulfate. In certain other embodiments, $R^8$ of Formula II is acetate.

In certain embodiments, at least one of $R^1$, $R^5$ or $R^8$ of Formula II is acetate. In other embodiments, at least two of $R^1$, $R^5$ or $R^8$ of Formula II are acetate. In particular embodiments, each of $R^1$, $R^5$ and $R^8$ of Formula II is acetate.

In other embodiments, the present invention provides a compound of Formula III:

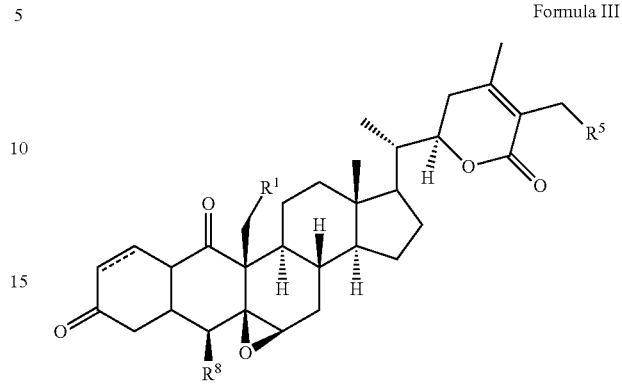

Formula III or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)—CH(R^C)—N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ≈ denotes a single or double bond.

In another embodiment, the present invention provides a compound of Formula IV:

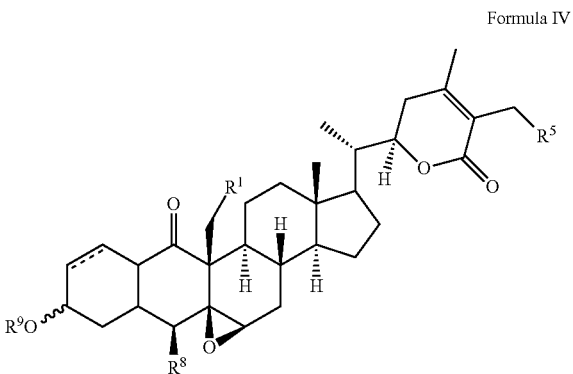

Formula IV or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$CH(R^C)—N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ and $R^9$ are each independently hydrogen or $-OR^D$, where each occurrence of $R^D$ is independently hydrogen, $-SO_3H$, $-PO_3H_2$, $-C(=O)R^C$, $-C(=O)N(R^C)_2$, $-CO_2R^C$, $-SOR^C$, $-SO_2R^C$ or $-C(R^C)_3$;

---- denotes a single or double bond; and

~~~ denotes either a | (β-stereochemistry) or ⋮ (α-stereochemistry).

In still other embodiments, the present invention provides a compound of Formula V:

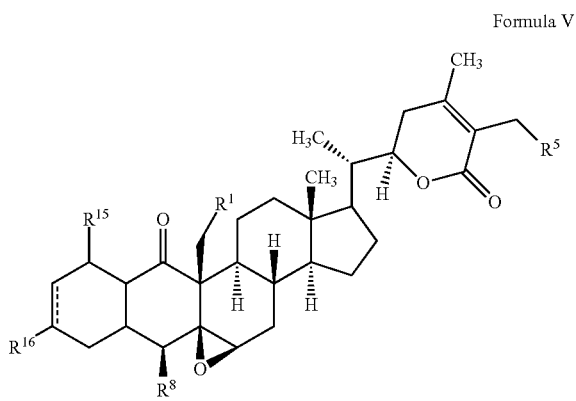

Formula V or a pharmaceutically acceptable salt or prodrug thereof, wherein $R^1$ and $R^8$ are each $-OR^B$, wherein each occurrence of $R^B$ is independently hydrogen, $-SO_3H$, $-PO_3H_2$, $-C(=O)R^C$, $-C(=O)-CH(R^C)-N(R^C)_2$, $-C(=O)N(R^C)_2$, $-CO_2R^C$, $-SOR^C$, $-SO_2R^C$, or $-C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or $-OR^D$, where $R^D$ is hydrogen, $-SO_3H$, $-PO_3H_2$, $-C(=O)R^C$, $-C(=O)N(R^C)_2$, $-CO_2R^C$, $-SOR^C$, $-SO_2R^C$ or $-C(R^C)_3$;

$R^{15}$ and $R^{16}$ are each independently $-OR^E$, where each occurrence of $R^E$ is independently a hydrogen, aliphatic group, aryl group, or $-SiR^C$, wherein $R^C$ is as defined above; and ---- denotes a single or double bond.

In yet other embodiments, the present invention provides a compound of Formula VI:

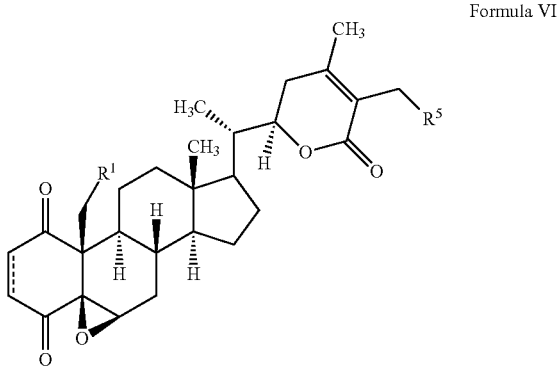

Formula VI or a pharmaceutically acceptable salt or prodrug thereof, wherein $R^1$ is $-OR^B$, wherein $R^B$ is hydrogen, $-SO_3H$, $-PO_3H_2$, $-C(=O)R^C$, $-C(=O)-CH(R^C)-N(R^C)_2$, $-C(=O)N(R^C)_2$, $-CO_2R^C$, $-SOR^C$, $-SO_2R^C$, or $-C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or $-OR^D$, where $R^D$ is hydrogen, $-SO_3H$, $-PO_3H_2$, $-C(=O)R^C$, $-C(=O)N(R^C)_2$, $-CO_2R^C$, $-SOR^C$, $-SO_2R^C$ or $-C(R^C)_3$; and ---- denotes a single or double bond.

In further embodiments, the present invention provides a compound of Formula VII:

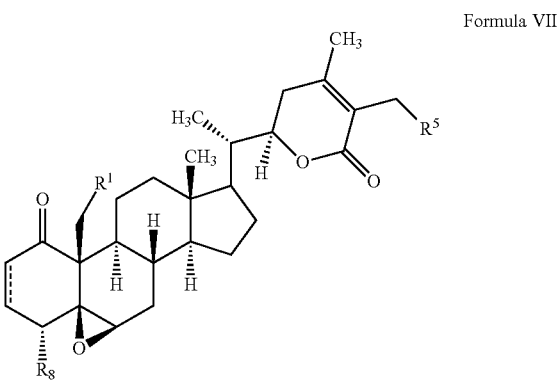

Formula VII or a pharmaceutically acceptable salt or prodrug thereof, wherein $R^1$ and $R^8$ are each $-OR^B$, wherein each occurrence of $R^B$ is independently hydrogen, $-SO_3H$, $-PO_3H_2$, $-C(=O)R^C$, $-C(=O)-CH(R^C)-N(R^C)_2$, $-C(=O)N(R^C)_2$, $-CO_2R^C$, $-SOR^C$, $-SO_2R^C$, or $-C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or $-OR^D$, where $R^D$ is hydrogen, $-SO_3H$, $-PO_3H_2$, $-C(=O)R^C$, $-C(=O)N(R^C)_2$, $-CO_2R^C$, $-SOR^C$, $-SO_2R^C$ or $-C(R^C)_3$; and ---- denotes a single or double bond.

The present invention also provides a compound of Formula VIII:

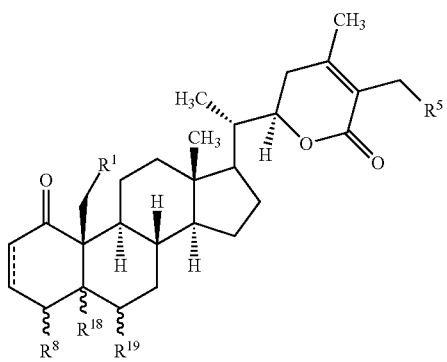

Formula VIII or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$;

$R^{18}$ and $R^{19}$ are each independently $R^H$ or —$OR^B$ as defined above, where $R^{20}$ is a halogen, alkyl group, alkenyl group (vinyl, propenyl, or allyl), aryl group, carboxylic acid group, amino group, alkylamino group, dialkylamino group, cyano group, azido group, hydroxylamino group, O-alkylhydroxylamino group;

==== denotes a single or double bond; and

⌇⌇⌇ denotes either a ∣ (β-stereochemistry) or ⦙ (α-stereochemistry).

The present invention also provides a compound of Formula IX:

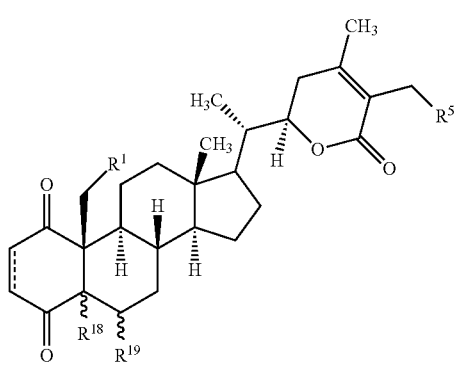

Formula IX or a pharmaceutically acceptable salt or prodrug thereof, wherein $R^1$ is —$OR^B$, wherein $R^B$ is hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$;

$R^{18}$ and $R^{19}$ are each independently $R^{20}$ or —$OR^B$ as defined above, where $R^{20}$ is independently a halogen, alkyl group, alkenyl group (vinyl, propenyl, or allyl), aryl group, carboxylic acid group, amino group, alkylamino group, dialkylamino group, cyano group, azido group, hydroxylamino group, O-alkylhydroxylamino group; and ==== denotes a single or double bond; and ⌇⌇⌇ denotes either a ∣ (β-stereochemistry) or ⦙ (α-stereochemistry).

A compound of Formula X is also embraced by the present invention:

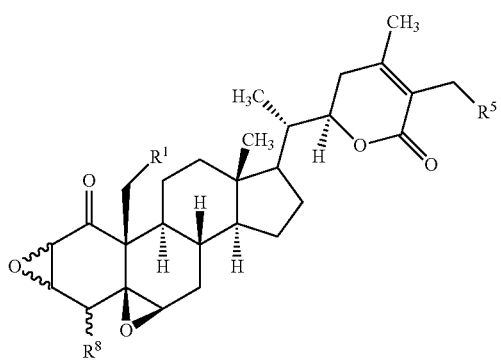

Formula X or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ⌇⌇⌇ denotes either a ∣ (β-stereochemistry) or ⦙ (α-stereochemistry).

A compound of Formula XI is also provided:

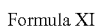
Formula XI

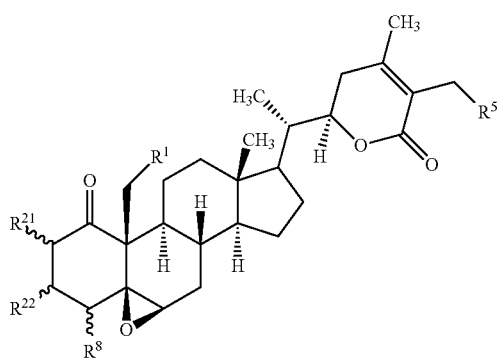

or a pharmaceutically acceptable salt or prodrug thereof, wherein $R^1$, $R^8$, $R^{21}$ and $R^{22}$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)$ wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ⌇⌇⌇ denotes either a ▮ (β-stereochemistry) or ⋮ (α-stereochemistry).

A compound of Formula XII is also embraced by the present invention:

Formula XII

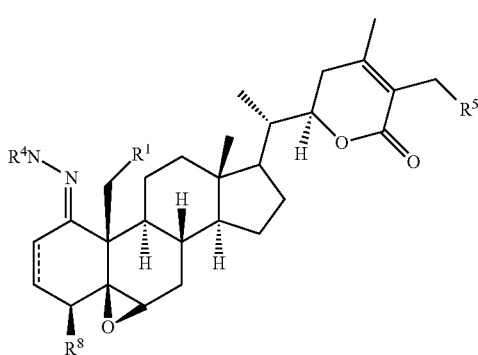

or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^4$ is hydrogen or an alkyl group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ---- denotes a single or double bond.

A compound of Formula XIII is also embraced by the present invention:

Formula XIII

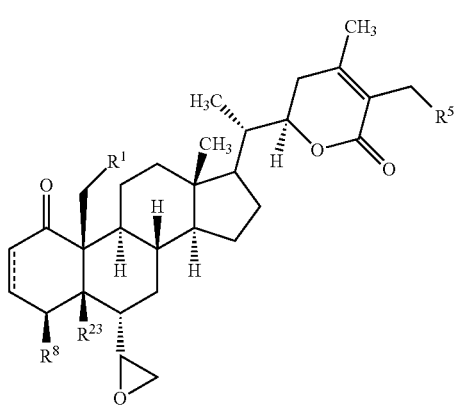

or a pharmaceutically acceptable salt or prodrug thereof, wherein $R^1$, $R^8$ and $R^{23}$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ---- denotes a single or double bond.

In particular embodiments, the present invention provides a compound of Formula XIV:

Formula XIV

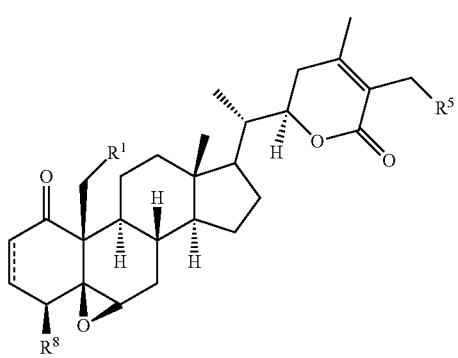

or a pharmaceutically acceptable salt or prodrug thereof, wherein $R^1$ and $R^8$ are each independently —CHO, —COOH, or COOR$^4$, wherein $R^4$ is hydrogen or an alkyl group;

$R^5$ is hydrogen or —$OR^D$, where $R^D$ is hydrogen, —$SO_3H$, —$PO_3H_2$, —C(=O)$R^C$, —C(=O)N($R^C$)$_2$, —$CO_2R^C$, —$SOR^C$, —$SO_2R^C$ or —$C(R^C)_3$; and ≈≈≈ denotes a single or double bond.

In a further embodiment, the present invention provides a compound of Formula XV:

Formula XV

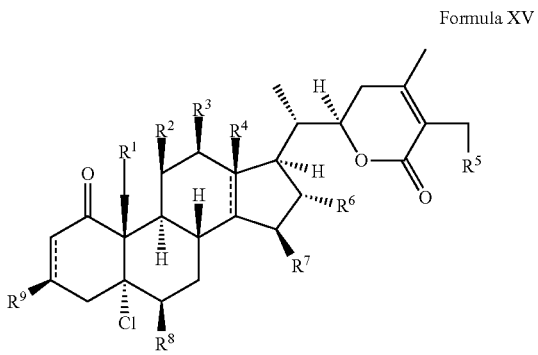

or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^2$, $R^3$, $R^5$, $R^7$ and $R^9$ are each independently hydrogen or —$OR^D$, where each occurrence of $R^D$ is independently hydrogen, —$SO_3H$, —$PO_3H_2$, —C(=O)$R^C$, —C(=O)N($R^C$)$_2$, —$CO_2R^C$, —$SOR^C$, —$SO_2R^C$ or —$C(R^C)_3$;

$R^4$ is hydrogen or an alkyl group;

$R^6$ is hydrogen or —OH; and

≈≈≈ denotes a single or double bond.

In a particular embodiment, the present invention provides a compound of Formula XVI:

Formula XVI

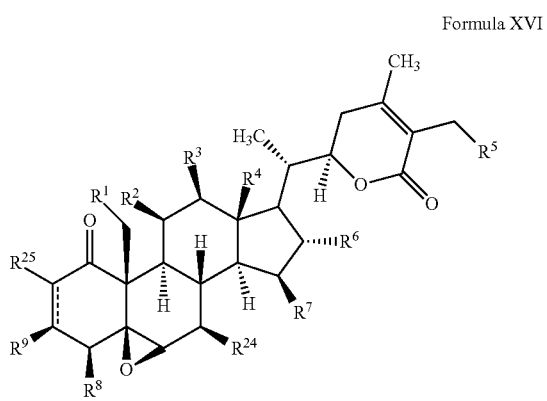

or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^2$, $R^3$, $R^5$, $R^7$ and $R^9$ are each independently hydrogen or —$OR^D$, where each occurrence of $R^D$ is independently hydrogen, —$SO_3H$, —$PO_3H_2$, —C(=O)$R^C$, —C(=O)N($R^C$)$_2$, —$CO_2R^C$, —$SOR^C$, —$SO_2R^C$ or —$C(R^C)_3$;

$R^4$ is hydrogen or an alkyl group;

$R^6$ is hydrogen or —OH;

$R^{24}$ is —OH or —OAc;

$R^{25}$ is I, aryl, or heteroaryl; and

≈≈≈ denotes a single or double bond.

In yet a further embodiment, the present invention provides a compound of Formula XVII:

Formula XVII

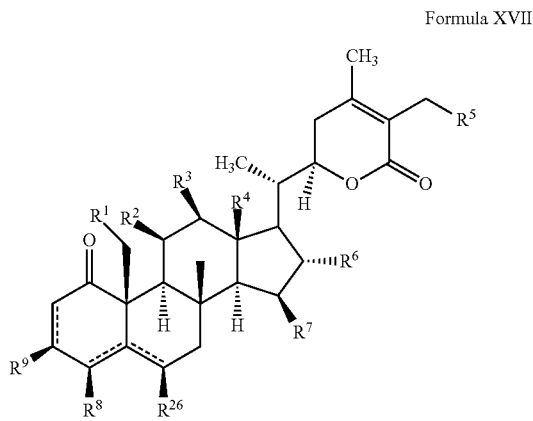

or a pharmaceutically acceptable salt or prodrug thereof, wherein $R^1$ is —$OR^B$, wherein $R^B$ is hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —$C(R^C)$ wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^2$, $R^3$, $R^5$ and $R^7$ are each independently hydrogen or —$OR^D$, where each occurrence of $R^D$ is independently hydrogen, —$SO_3H$, —$PO_3H_2$, —C(=O)$R^C$, —C(=O)N($R^C$)$_2$, —$CO_2R^C$, —$SOR^C$, —$SO_2R^C$ or —$C(R^C)_3$;

$R^4$ is hydrogen or an alkyl group;

$R^6$ is hydrogen or —OH;

$R^8$ and $R^9$ are hydrogen;

$R^{26}$ is —OH or —OAc; and

≈≈≈ denotes a single or double bond.

It will be appreciated that the compounds of the present invention, as described herein, may be substituted with any number of substituents or functional moieties. In general, the term "substituted," whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thioxo, cyano, isocyano, amino, azido, nitro, hydroxyl, thiol, halo, etc.), and any combination thereof (for example, aliphaticamino, heteroaliphaticamino, alkylamino, heteroalkylamino, acylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety. The term "stable moiety," as used herein, preferably refers to a moiety which possess stability sufficient to allow manufacture, and which maintains its integrity for a sufficient period of time to be useful for the purposes detailed herein.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

With particular reference to the compounds herein, the term "acyl," as used herein, refers to a group having the general formula $-C(=O)R^F$, $-C(=O)OR^F$, $-C(=O)-O-C(=O)R^F$, $-C(=O)SR^F$, $-C(=O)N(R^F)_2$, $-C(=S)R^F$, $-C(=S)N(R^F)_2$, and $-C(=S)S(R^F)$, $-C(=NR^F)R^F$, $-C(=NR^F)OR^F$, $-C(=NR^F)SR^F$, and $-C(=NR^F)N(R^F)_2$, wherein $R^F$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^E$ groups taken together form a 5- to 6-membered heterocyclic ring. Exemplary acyl groups include aldehydes ($-$CHO), carboxylic acids ($-$CO$_2$H), ketones, acyl esters, amides, imines, carbonates, carbamates, and ureas. Acyl substituents include, but are not limited to, any of the substituents described herein, that result in the formation of a stable moiety.

The term "acyloxy" refers to a "substituted hydroxyl" of the formula ($-$OR$^G$), wherein R$^G$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein.

The term "alkyl," refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein.

The term "alkenyl," denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein.

The term "alkynyl," refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-carbon atoms. In still other embodiments, the alkynyl group contains 2-8 carbon atoms. In still other embodiments, the alkynyl group contains 2-5 carbon atoms.

Representative alkynyl groups include, but are not limited to, ethynyl, 2-propynyl(propargyl), 1-propynyl, and the like, which may bear one or more substituents. Alkynyl group substituents include, but are not limited to, any of the substituents described herein.

The term "amino," refers to a group of the formula (—NH$_2$). A "substituted amino" refers either to a mono-substituted amine (—NHR$^H$) of a disubstituted amine (—NR$^H_2$), wherein the R$^H$ substituent is, independently, a hydrogen or an optionally substituted alkyl group, as defined herein. In certain embodiments, the R$^H$ substituents of the di-substituted amino group (—NR$^H_2$) form a 5- to 6-membered heterocyclic ring.

The term "alkoxy" refers to a "substituted hydroxyl" of the formula (—OR$^I$), wherein R$^I$ is an optionally substituted alkyl group, as defined herein, and the oxygen moiety is directly attached to the parent molecule.

The term "alkylthioxy" refers to a "substituted thiol" of the formula (—SR$^J$), wherein R$^J$ is an optionally substituted alkyl group, as defined herein, and the sulfur moiety is directly attached to the parent molecule.

The term "alkylamino" refers to a "substituted amino" of the formula (—NR$^K_2$), wherein R$^K$ is, independently, a hydrogen or an optionally substituted alkyl group, as defined herein, and the nitrogen moiety is directly attached to the parent molecule.

The term "aryl" refers to stable aromatic mono- or polycyclic ring systems having 3-20 ring atoms, of which all the ring atoms are carbon, and which may be substituted or unsubstituted. In certain embodiments of the present invention, "aryl" refers to a mono, bi, or tricyclic C$_4$-C$_{20}$ aromatic ring system having one, two, or three aromatic rings which include, but not limited to, phenyl, biphenyl, naphthyl, and the like, which may bear one or more substituents.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—OR$^L$), wherein R$^L$ is an optionally substituted aryl group, as defined herein, and the oxygen moiety is directly attached to the parent molecule.

The term "arylamino" refers to a "substituted amino" of the formula (—NR$^M_2$), wherein R$^M$ is, independently, a hydrogen or an optionally substituted aryl group, as defined herein, and the nitrogen moiety is directly attached to the parent molecule.

The term "arylthioxy" refers to a "substituted thiol" of the formula (—SR$^N$), wherein R$^N$ is an optionally substituted aryl group, as defined herein, and the sulfur moiety is directly attached to the parent molecule.

The term "azido," as used herein, refers to a group of the formula (—N$_3$).

The term "cyano," as used herein, refers to a group of the formula (—CN).

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl groups. Thus, the term "heteroaliphatic" includes the terms "heteroalkyl," "heteroalkenyl," "heteroalkynyl" and the like. Furthermore, as used herein, the terms "heteroalkyl," "heteroalkenyl," "heteroalkynyl" and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. The terms "heteroalkyl," "heteroalkenyl" and "heteroalkynyl" respectively refer to an alkyl, alkenyl and alkynyl groups, as defined herein, which contain one or more oxygen, sulfur, nitrogen, phosphorus, or silicon atoms, e.g., in place of carbon atoms.

The term "heteroalkylamino" refers to a "substituted amino" of the formula (—NR$^O_2$), wherein R$^O$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^P$), wherein R$^P$ is an optionally substituted heteroalkyl group, as defined herein, and the oxygen moiety is directly attached to the parent molecule.

The term "heteroalkylthioxy" refers to a "substituted thiol" of the formula (—SR$^Q$), wherein R$^Q$ is an optionally substituted heteroalkyl group, as defined herein, and the sulfur moiety is directly attached to the parent molecule.

The term "heterocyclic," "heterocycles," or "heterocyclyl" refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents as described herein.

The term "heteroaryl" refers to stable aromatic mono- or polycyclic ring systems having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents as described herein.

The term "heteroarylene" refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein.

The term "heteroarylamino" refers to a "substituted amino" of the ($-NR^R_2$), wherein $R^R$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula ($-OR^S$), wherein $R^S$ is an optionally substituted heteroaryl group, as defined herein, and the oxygen moiety is directly attached to the parent molecule.

The term "heteroarylthioxy" refers to a "substituted thiol" of the formula ($-SR^T$), wherein $R^T$ is an optionally substituted heteroaryl group, as defined herein, and the sulfur moiety is directly attached to the parent molecule.

The term "hydroxyl" or "hydroxyl" refers to a group of the formula ($-OH$). A "substituted hydroxyl" refers to a group of the formula ($-OR^U$), wherein $R^U$ can include, but is not limited to, aliphatic, alkyl, alkenyl, alkynyl, heteroaliphatic, heterocyclic, aryl, heteroaryl, acyl, nitro, alkylaryl, and arylalkyl groups, each of which may or may not be further substituted.

The term "imino" refers to a group of the formula ($=NR^V$), wherein $R^V$ corresponds to hydrogen or any substitutent, including, e.g., aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted. In certain embodiments, imino refers to $=NH$ wherein $R^V$ is hydrogen.

The term "isocyano" refers to a group of the formula ($-NC$). The term "nitro" refers to a group of the formula ($-NO_2$). The term "oxo" refers to a group of the formula ($=O$).

In certain embodiments of the inventions, ==== is a double bond. In other embodiments ---- is a single bond.

Exemplary compounds of the invention are provided in the Examples. The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Where an isomer/enantiomer is preferred, it may, in some embodiments, be provided substantially free of the corresponding enantiomer, and may also be referred to as "optically enriched." "Optically enriched" means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al. (1981) *Enantiomers, Racemates and Resolutions*, Wiley Interscience, New York; Wilen, et al. (1977) *Tetrahedron* 33:2725.

Pharmaceutically acceptable salts of the instant compounds are also embraced by the present invention. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. For example, Berge, et al. ((1977) *J. Pharmaceutical. Sciences* 66:1-19) describe pharmaceutically acceptable salts in detail. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In addition to pharmaceutically acceptable salts, prodrugs of the instant compounds are also provided. As used herein, a prodrug is intended to mean derivatizing a compound of the invention by coupling the compound with an amino acid(s), peptide(s) and/or protein(s) to increase biological distribution to the site of action. Chiral amino acids and/or peptides enhance efficient distribution to the site of action and improve the solubility of the drug in formulations. When the prodrug is cleaved by an enzyme (e.g., an endogenous peptidases) at the coupled group, the prodrug is transformed into an active drug plus an endogenous amino acid(s) and/or peptide(s), and therefore will not add any foreign substance/toxin to the system, other than the drug. In addition, prodrugs can be further modified to increase water solubility by converting the prodrug into an appropriate salt by reacting the prodrug with an acid (mineral or organic).

A compound of the invention can be isolated from *P. longifolia*, produced semi-synthetically from natural products of *P. longifolia*, or wholly synthetically produced. When isolated from *P. longifolia*, desirably the compound is isolated from the aerial tissue and/or roots of *P. longifolia*. Aerial tissues of *P. longifolia* can be extracted with a solvent to give the crude natural product extract. In certain embodiments, the solvent includes an alcohol such as methanol. In another embodiment, the solvent includes dichloromethane. In particular embodiments, the solvent is a mixture of methanol and dichloromethane.

In certain embodiments, the crude natural product extract obtained from *P. longifolia* is purified. In certain embodiments, the extract is purified by chromatography. In certain embodiments, the extract is purified by silica gel chromatography. In certain embodiments, the crude extract is purified by successive rounds of chromatography. HPLC may be used to purify the desired compounds. The desired natural product can optionally be further purified by crystallization. The purified compounds may be characterized by various analytical methods including elemental analysis, mass spectrometry, IR, UV/vis, NMR, and x-ray crystallography. Desirably, the compound is purified to homogeneity (100%) or near homogeneity (90 to 95%).

In some embodiments, novel withanolides (e.g., X002 and X003) are synthesized from withanolide natural products. In certain embodiments, novel withanolides are synthesized from X001. As described herein, diacetyl and triacetyl analogs of X001 can be synthesized using an aceylation procedure. A suitable acetylating agent, for example, is acetic anhydride.

Particularly useful compounds of the present invention include those with biological activity (e.g., anti-proliferative and/or cytotoxic activity). In this respect, the present invention features pharmaceutical compositions containing the compounds described herein or and their use in treating disease in a human or non-human animal. The term "subject," as used herein, refers to any animal. In certain embodiments, the subject is a mammal. In certain embodiments, the term "subject" refers to a human (e.g., a man, a woman, or a child). The term "administer," "administering," or "administration" refers to implanting, absorbing, ingesting, injecting, or inhaling the inventive compound.

It is contemplated that, similar to other withanolides, the compounds of the present invention will activate the heat shock network. Thus, in certain embodiments, the present invention provides a method for treating a heat shock network-associated disorder by administering to a subject in need thereof a compound of the present invention or pharmaceutically acceptable composition thereof. As used herein, the term "heat shock network-associated disorder" means any disease or other deleterious condition in which the heat shock network is known to play a role. Accordingly, another embodiment of the present invention relates to treating or lessening the severity of one or more diseases in which the heat shock network is known to play a role including, but not limited to, autoimmune diseases as well as Huntington's disease, Parkinson's disease, Alzheimer's disease, and other disorders associated with protein misfolding and/or aggregation.

It is further contemplated that the inventive compounds will alter the actin bundling activity of annexin II. Thus, in certain embodiments, the present invention provides a method for treating an annexin II-mediated disorder by administering to a subject in need thereof a compound of the present invention or pharmaceutically acceptable composition thereof. As used herein, the term "annexin II-mediated disorder" means any disease or other deleterious condition in which annexin II is known to play a role. Accordingly, another embodiment of the present invention relates to treating or lessening the severity of one or more diseases in which annexin II is known to play a role including, but not limited to, atherosclerosis, diabetes, disorders associated with pathological proliferation of blood vessels such as diabetic retinopathy, macular degeneration, and cancers, e.g., glioma, colorectal carcinoma, gastric carcinoma, hepatic carcinoma, small cell lung carcinoma, and pancreatic carcinoma.

Inhibition of the 20S proteasome is also an activity of withanolides. Thus, in certain embodiments, the present invention provides a method for treating a 20S proteasome-mediated disorder by administering to a subject in need thereof a compound of the present invention or pharmaceutically acceptable composition thereof. As used herein, the term "20S proteasome-mediated disorder" means any disease or other deleterious condition in which the 20S proteasome is known to play a role. Accordingly, another embodiment of the present invention relates to treating or lessening the severity of one or more diseases in which the 20S proteasome is known to play a role including, but not limited to, multiple myeloma, pancreatic cancers, B-cell related cancers such as non-Hodgkin's lymphoma, glioma, and autoimmune diseases.

Certain inventive compounds are also expected to inhibit the intermediate filament protein vimentin. Thus, in certain embodiments, the present invention provides a method for treating a vimentin-mediated disorder by administering to a subject in need thereof a compound of the present invention or pharmaceutically acceptable composition thereof. As used herein, the term "vimentin-mediated disorder" means any disease or other deleterious condition in which vimentin is known to play a role. Accordingly, another embodiment of the present invention relates to treating or lessening the severity of one or more diseases in which vimentin is known to play a role including, but not limited to, autoimmune diseases, organ transplantation, vascular disease, and giant axonal neuropathy.

One or more compounds of the present invention are also expected to inhibit NFκB activation. Thus, in certain embodiments, the present invention provides a method for treating NFκB-mediated disorders by administering to a subject in need thereof a compound of the present invention or pharmaceutically acceptable composition thereof. As used herein, the term "NFκB-mediated disorder" means any disease or other deleterious condition in which NFκB is known to play a role. Accordingly, another embodiment of the present invention relates to treating or lessening the severity of one or more diseases in which NFκB activation is known to play a role including, but not limited to, rheumatoid arthritis, inflammatory bowel disease, asthma and other inflammatory disorders, as well as cancers such as leukemia, lymphoma, colon cancer, and ovarian cancer.

Withanolides are also known to inhibit protein kinase C (PKC). Thus, in certain embodiments, the present invention provides a method for treating a PKC-mediated disorder by administering to a subject in need thereof a compound of the present invention or pharmaceutically acceptable composition thereof. As used herein, the term "PKC-mediated disorder" means any disease or other deleterious condition in which PKC is known to play a role. Accordingly, another embodiment of the present invention relates to treating or lessening the severity of one or more diseases in which PKC is known to play a role including, but not limited to, Alzheimer's disease, diabetic vascular disease, glaucoma, lung cancer, colon cancer, renal cell cancer, hepatocellular cancer, prostate cancer, ovarian cancer, bladder cancer, and brain cancer.

In particular, compounds of the invention were found to induce apoptosis in the absence of necrosis. Thus, in certain embodiments, the present invention provides a method for treating a disorder in which apoptosis is known to play a role by administering to a subject in need thereof a compound of the present invention or pharmaceutically acceptable composition thereof. In accordance with this embodiment, subjects benefiting from treatment will exhibit a lessening or amelioration of the severity of one or more diseases in which apoptosis is known to play a role including, but not limited to, autoimmune diseases and cancer.

The compounds and pharmaceutical compositions of the present invention may be used in treating or preventing any disease or condition including, but not limited to, asthma, arthritis, inflammatory diseases (e.g., Crohn's disease, rheumatoid arthritis, psoriasis), proliferative diseases (e.g., cancer, benign neoplasms, diabetic retinopathy), cardiovascular diseases, neurodegenerative diseases, protein aggregation disorders (e.g., Huntington's disease, Alzheimer's disease), and autoimmune diseases (e.g., rheumatoid arthritis, lupus). The inventive compounds and pharmaceutical compositions may be administered to animals, preferably mammals (e.g., domesticated animals, cats, dogs, mice, rats), and more preferably humans. Any method of administration may be used to deliver the inventive compound or pharmaceutical composition to the animal. In certain embodiments, the compound or pharmaceutical composition is administered orally. In other embodiments, the compound or pharmaceutical composition is administered parenterally.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The invention further relates to a method for treating, ameliorating, or preventing cellular neoplasia by administration of an effective amount of a compound according to this invention to a mammal, in particular a human in need of such treatment. A "neoplasia" is defined by cells displaying aberrant cell proliferation and/or survival and/or a block in differentiation. The term "neoplasia" includes benign neoplasia, which is described by hyperproliferation of cells, incapable of forming an aggressive, metastasizing tumor in vivo, and, in contrast, malignant neoplasia, which is described by cells with multiple cellular and biochemical abnormalities, capable of forming a systemic disease, for example forming tumor metastases in distant organs.

Compounds according to this invention can be particularly used for the treatment of malignant neoplasia, also described as cancer, characterized by tumor cells finally metastasizing into distinct organs or tissues. Examples of malignant neoplasia treated with compounds according to the present invention include solid and hematological tumors. Solid tumors are exemplified by tumors of the breast, bladder, bone, brain, central and peripheral nervous system, colon, connective tissue, endocrine glands (e.g., thyroid and adrenal cortex), esophagus, endometrium, germ cells, head and neck, kidney, liver, lung, larynx and hypopharynx, mesothelioma, muscle, ovary, pancreas, prostate, rectum, renal, small intestine, soft tissue, testis, stomach, skin, ureter, vagina, and vulva. Malignant neoplasia includes inherited cancers exemplified by retinoblastoma and Wilms tumor. In addition, malignant neoplasia includes primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), chronic lymphocytic leukemia (CLL), Hodgkins disease, multiple myeloma, and T-cell lymphoma. Also included are myelodysplastic syndrome, plasma cell neoplasia, paraneoplastic syndromes, and cancers of unknown primary site as well as AIDS-related malignancies.

It will also be appreciated that a cancer (malignant neoplasia) as a life-threatening disease process does not necessarily require the formation of metastases in distant organs. Certain tumors exert devastating effects on the primary organ itself through their aggressive growth properties. These can lead to the destruction of the tissue and organ structure finally resulting in failure of the assigned organ function.

In certain embodiments, the present invention provides a method for the treatment of benign neoplasia. Examples of benign neoplasia treated with compounds according to the present invention include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In other embodiments, the present invention provides methods for treating or lessening the severity of autoimmune diseases including, but not limited to, inflammatory bowel disease, arthritis, systemic lupus erythematosus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, the present invention provides a method for treating or lessening the severity of one or more diseases and conditions, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Behcet's disease, Blau syndrome, blepharitis, bronchiolitis, bronchitis, bursitis, cervicitis, cholangitis, cholecystitis, chronic recurrent multifocal osteomyelitis (CRMO), colitis, conjunctivitis, cryopyrin associated periodic syndrome (CAPS), cystitis, dacryoadenitis, dermatitis, dermatomyositis, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, uveitis, vaginitis, vasculitis, or vulvitis.

In certain embodiments, the present invention provides methods for treating or lessening the severity of arthropathies and osteopathological diseases including, but not limited to, rheumatoid arthritis, osteoarthritis, gout, polyarthritis, and psoriatic arthritis.

In particular embodiments, the present invention provides methods for treating or lessening the severity of hyperproliferative diseases including, but not limited to, psoriasis or smooth muscle cell proliferation including vascular proliferative disorders, atherosclerosis, and restenosis. In certain embodiments, the present invention provides methods for treating or lessening the severity of endometriosis, uterine fibroids, endometrial hyperplasia and benign prostate hyperplasia.

In certain embodiments, the present invention provides methods for treating or lessening the severity of acute and chronic inflammatory diseases and dermal diseases including, but not limited to, ulcerative colitis, inflammatory bowel disease, Crohns disease, allergic rhinitis, allergic dermatitis, cystic fibrosis, chronic obstructive bronchitis, and asthma.

In some embodiments, the present invention provides a method for treating or lessening the severity of a cardiovascular disorder including, but not limited to, myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis, ischemic stroke, cardiac hypertrophy and heart failure.

In certain embodiments, the present invention provides methods for treating or lessening the severity of neurodenerative disorders and/or protein aggregation disorders including, but not limited to, Parkinson's disease, Alzheimer's disease or polyglutamine-related disorders including, but not limited to, Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA), Dentatorubral pallidolusyian atrophy (DRPLA), fronto-temporal dementia, Lewy body disease, Pick's disease, and progressive supranuclear palsy (PSP).

In some embodiments, the invention provides methods of treating a subject in need of neuroprotection. In some embodiments, the subject has suffered a stroke, seizure, or traumatic injury to the nervous system or has suffered exposure to a toxic agent, e.g., a neurotoxic agent. For example, in some embodiments the subject has suffered a spinal cord injury. In some embodiments, the subject has suffered or is expected to suffer oxidative stress to the nervous system or a portion thereof (e.g., the central nervous system (CNS) or a portion thereof (e.g., brain, brain region, spinal cord)), or the peripheral nervous system (PNS) or a portion thereof, such as one or more nerves or nerve trunks. In some embodiments, said nerve is a cranial nerve. In some embodiments said oxidative stress is caused at least in part by exposure of the subject to a toxic agent, e.g., a neurotoxin. In some embodiments, the toxic agent is a chemical compound. A chemical compound can be, e.g., a polypeptide, nucleic acid, small organic molecule, etc. A chemical compound can be invented by man or can be a naturally occurring compound. In some embodiments, the toxic agent is an infectious agent or a substance produced by an infectious agent (e.g., a bacterium) or encoded in its genome. In some embodiments the toxic agent is a virus, e.g., a neurotropic virus. In some embodiments the subject has suffered or is expected to suffer an event that causes oxygen deprivation, nutrient (e.g., glucose) deprivation, and/or growth factor deprivation of nervous system cells. In some embodiments the subject has suffered a hemorrhagic event in the nervous system, e.g., a hemorrhagic stroke, subarachnoid hemorrhage, or aneurysm. In some embodiments a subject suffers from or is at increased risk of (e.g., has one or more art-recognized risk factors for) a disease or condition characterized by neuronal deterioration or loss, e.g., a neuropathy. In some embodiments the subject suffers or is at increased risk of diabetes (e.g., diabetic neuropathy), motor neuron disease, or glaucoma. In some embodiments, administering a compound of the invention inhibits at least some death (e.g., apoptosis) and/or deterioration of nervous system cells that would otherwise occur, e.g., the invention protects at least some nervous system cells from undergoing death or deterioration. In some embodiments, said nervous system cells comprise neuronal cells (also termed "neurons"). A neuronal cell is often characterized, at least in part, by containing one or more markers of neuronal differentiation. Such a marker can be, for example, a neurofilament (e.g., heavy (NF-H), medium (NF-M) or light neurofilament (NF-L) proteins, nestin and α-internexin) NeuN, or MAP2. A neuronal cell further is often characterized as having one or more cell processes (e.g., axon, dendrite). In some embodiments, said nervous system cells comprise glial cells, e.g., astrocytes, oligodendrocytes, and/or microglia. Without wishing to be bound by theory, such non-neuronal nervous system cells may secrete neurotrophic factors or otherwise promote survival and/or inhibit deterioration of neuronal cells. For example, such cells, e.g., astrocytes, may secrete one or more anti-oxidants or antioxidant precursors. In some embodiments, the invention provides a method of providing an acute neuroprotective effect by administering a compound of the invention close to the time of acute nervous system insult (e.g., stroke, seizure, injury, toxin exposure), thereby producing an acute neuroprotective effect in at least some neuronal cells. In some embodiments said administration occurs prior to, e.g., within 2 hours, 4 hours, or 6 hours prior to occurrence of the insult. In some embodiments said administration occurs within 24 hours or within 48 hours prior to occurrence of the insult. For example, a compound may be administered before a surgical procedure that is expected to result in neuronal damage, oxygen or nutrient deprivation, or otherwise have deleterious effects on the nervous system and/or before administration of a therapeutic agent that may have such an effect (e.g., as an undesired "side effect"). In some embodiments said administration occurs subsequent to, e.g., within 2 hours, 4 hours, or 6 hours after occurrence of the insult. In some embodiments, said administration occurs within 24 hours or within 48 hours after occurrence of the insult. In some embodiments administration occurs chronically, e.g., the compound is administered multiple times (or continuously) over a time period of at least 6 weeks, e.g., a period of at least 6 weeks after occurrence of the insult. In some embodiments, a neuroprotective effect is evident within 24 hours, or within 48 hours, after administration of a compound, e.g., the extent of neuronal death or deterioration is reduced relative to what would be expected had the compound not been administered. In some embodiments, neuronal death, e.g., apoptosis, is reduced by at least 20%, e.g., by between 20% and 90%, e.g., by between 40% and 80%, e.g., by between 50% and 75%. If desired, cell viability and/or apoptosis may be assessed using a variety of assays known in the art. In some embodiments, neuroprotection according to the inventive methods results in an improved functional outcome relative to what would be otherwise expected (e.g., relative to a control). In some embodiments, the invention provides a method of inhibiting neuronal excitotoxicity, e.g., excitotoxicity induced by an excitatory amino acid such as NMDA or glutamate (e.g., an abnormally elevated level or sudden release of large amounts of such amino acid(s)). In some embodiments, the invention provides a method of inhibiting ischemic reperfusion injury. In some embodiments, a compound according to the invention provides a neurotrophic effect, e.g., promotes survival, development, and/or growth of neurons. In some embodiments, a compound according to the invention has an effect that at least in part mimics that of nerve growth factor (NGF), brain-derived neurotrophic factor (BDNF), ciliary neurotrophic factor (CNTF), neurotrophin-3 (NT-3), erythropoietin (EPO), and/or neurotrophin-4 (NT-4). In some embodiments, a compound according to the invention augments a deficiency of at least one of said neurotrophic factors and/or is administered together with one or more of said neurotrophic factors. In some embodiments, the invention provides a method of promoting neurite outgrowth and/or axonal outgrowth. In some embodiments, said promoting of neurite outgrowth and/or axonal outgrowth occurs in neurons that have been subjected to an injury that results in severing of an axon. In some embodiments, said promoting of neurite outgrowth and/or axonal outgrowth occurs in neurons that are at least in part deprived of a neurotrophic factor, e.g., BDNF-deprived. In some embodiments, the invention provides a method of enhancing peripheral axon and/or nerve regeneration, e.g., after a crush injury.

The present invention further includes a method for the treatment of mammals, including humans, which are suffering from one of the above-mentioned conditions, illnesses, disorders, or diseases. The method includes administration of a pharmacologically active and therapeutically effective amount of one or more of the compounds according to this invention, which function to induce various cellular effects, induce the heat shock response, arrest cell proliferation, induce cell differentiation, and/or induce apoptosis, to the subject in need of such treatment.

The invention further relates to the use of the compounds according to the present invention for the production of pharmaceutical compositions for inhibiting or treating cellular neoplasia, such as benign or malignant neoplasia, e.g., cancer; pharmaceutical compositions that activate the heat shock response; pharmaceutical compositions which can be used for treating, preventing, or ameliorating of diseases responsive to arresting aberrant cell growth, such as proliferative diseases of benign or malignant behavior, such as any of those diseases mentioned herein; pharmaceutical compositions which can be used for treating, preventing, or ameliorating of disorders responsive to induction of apoptosis, such as any of those diseases mentioned herein.

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well-known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, e.g., for treating cancer and/or when a pro-apoptotic effect is desired, a dose that is at or relatively close to the maximum tolerated dose (MTD) is used. In some embodiments, a dose between 50% and 100% of MTD may be used. In some embodiments, a dose between 75% and 100% of MTD may be used. In some embodiments, e.g., in methods of treating a neurodegenerative disease, providing neuroprotection, and/or promoting axonal and/or neurite outgrowth, a lower dose is used than in methods for treating cancer. In some embodiments, the dose for use in such methods is between 10- and 100-fold lower than the MTD and/or between 10- and 100-fold lower than the dose used in cancer. MTD can be determined using standard methods known to those skilled in the art.

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such CREMOPHOR, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable carriers and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle or carrier. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or fillers or extenders such as starches, lactose, sucrose, glucose, mannitol, and silicic acid; binders such as, for example, carboxymethylcellulose, alginates, gelatin, polyvinylpyrrolidinone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, cetyl alcohol and glycerol monostearate) absorbents such as kaolin and bentonite clay; and lubricants such as talc, calcium stearate, magnesium stearate, solid polyethylene glycols, sodium lauryl sulfate, and mixtures thereof. In the case of capsules, tablets and pills, the dosage form may also include buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients or carriers as noted above. The solid dosage forms of tablets, dragees, capsules, pills, and granules can be prepared with coatings and shells such as enteric coatings, release controlling coatings and other coatings well-known in the pharmaceutical formulating art. In such solid dosage forms the active protein may be admixed with at least one inert diluent such as sucrose, lactose or starch. Such dosage forms may also include, as is normal practice, additional substances other than inert diluents, e.g., tableting lubricants and other tableting aids such a magnesium stearate and microcrystalline cellulose. In the case of capsules, tablets, and pills, the dosage forms may also include buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, a method of local administration to the nervous system or a portion thereof is used to administer a compound according to the invention. In some embodiments a compound according to the invention is administered using an internal (implantable) or external pump system to deliver a compound according to the invention to the CNS. Such systems can include a reservoir from which continuous or intermittent release of a composition occurs into the target tissue or in the vicinity thereof, e.g., via a catheter. The pump may be programmed to release predetermined amounts at predetermined time intervals. See, e.g., U.S. Pat. No. 6,263,237. In some embodiments, a technique of regional delivery of therapeutic agents directly into brain parenchyma, such as intracerebral microinfusion, is used. In certain embodiments delivery is accomplished by surgically implanting a catheter through the skull so that the tip has access to a CSF-containing space. The other end of the catheter is then connected to a reservoir, which is placed beneath the scalp (subcutaneously). Methods for administering agents to the spinal cord, e.g., methods such as are commonly used in the treatment of chronic pain to deliver analgesic agents (e.g., intrathecal administration such as by injection) may be used in certain embodiments of the invention. If a pump is used, the catheter may be implanted so that the discharge portion lies in the intrathecal space while the other end is connected to the pump reservoir.

For local administration to the PNS, if desired, injection or infiltration into a nerve or nerve trunk, e.g., adjacent to a site of nerve damage or injury, may be used. Methods for administering anesthetic agents to diverse nerves, nerve bundles, etc., within the PNS are well known in the art, and are of use in various embodiments of the invention.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. For example, an inventive compound may be administered concurrently with another anticancer agent and/or with radiation in order to treat cancer. In some embodiments an inventive compound is administered concurrently with another neuroprotective agent in order to treat a subject in need of neuroprotection and/or concurrently with a procedure or process such as inducing hypothermia or hyperbaric oxygen treatment. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

In still another aspect, the present invention also provides a pharmaceutical pack or kit including one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

The invention is described in greater detail by the following non-limiting examples.

EXAMPLE 1

Extraction, Fractionation and Isolation of X001

Powdered *P. longifolia* plant material (934.39 g) was extracted with dichloromethane and methanol (1:1). The residue (106.8 g) from the extract was fractionated with partition between hexane and water. The aqueous layer was separated and further extracted with ethyl acetate and n-butanol. After removal of the solvent, the ethyl acetate fraction (21.9 g) obtained was applied to a silica gel flash chromatography column and the column was eluted with dichloromethane and methanol (97:3, 955 and 9:1). The fractions from dichloromethane:methanol (95:5) were subjected to TLC examination using dichloromethane:methanol (95:5) as developing solvent. The fractions with $R_f$ 0.56 that showed single spots were combined. The solvent was removed under reduced pressure to yield crude X001. The crude X001 was crystallized from ethyl acetate and hexane mixtures to yield pure X001 (Yield=1.53 grams). The X001 was re-crystallized using a mixture of chloroform and acetonitrile and suitable crystals were subjected to X-ray diffraction analysis. The structure of X001 was determined by spectral analysis including IR, UV, ESIMS, 1D and 2D NMR ($^1$H, $^{13}$C, $^1$H-$^1$H COSY, HSQC, HMBC, NOESY) and established from X-ray crystallography.

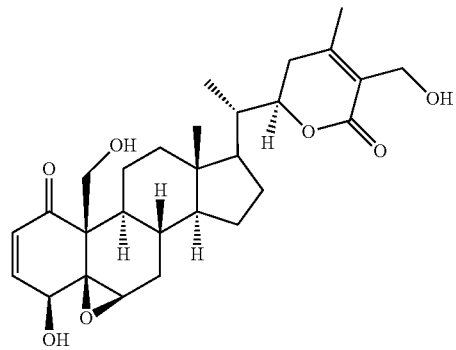

X001

In addition to X001, another 19-OH withanolide, X030B was isolated and characterized.

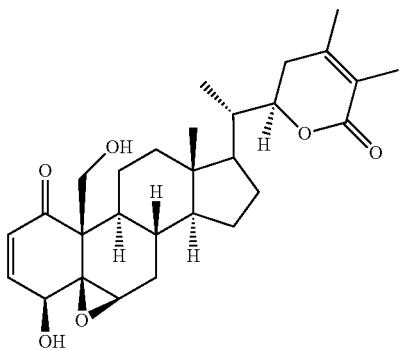

X030B

EXAMPLE 2

Diacetyl and Triacetyl Analogs of X001

X001 (50.6 mg) was taken into a dry 25-mL round bottom flask equipped with a magnetic stirrer. Dry pyridine (2 ml) and 2 ml of acetic anhydride were added to the flask and the contents were stirred at room temperature. The contents were kept stirring for additional three and half hours at room temperature.

Subsequently, the contents were poured onto cold water (5° C.) (25 ml) and extracted with ethyl acetate (3×10 mL) in a separatory funnel. The ethyl acetate layer was washed with cold brine (10 ml×3) and cold water (10 mL). The ethyl acetate layer was separated. The ethyl acetate layer was dried over anhydrous sodium sulfate and filtered. The solvent was removed under reduced pressure from the filtrate to get a residue (58.2 mg). HPLC examination showed two peaks and the residue was purified using preparative HPLC using reverse phase C-18 HPLC column and a gradient of acetonitrile and water. The fractions were collected from the two peaks. Removal of the solvent from the fractions gave white powder of X001-diacetate (14.7 mg) and X001-triacetate (16.3 mg). The structures were confirmed by spectral analysis.

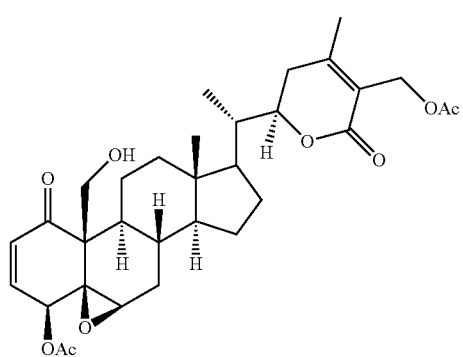

X002

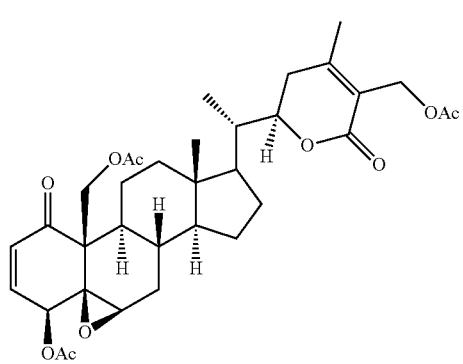

X003

(4,27-diactyl X001) (4,19,27-triacetyl X001)

The effect of X001 and diacetyl and triacetyl analogs thereof on cell viability was tested. Human carcinoid cells, NCI-H727 (ATCC, Manassas, Va.), were cultured under standard conditions. Squamous cell carcinoma of head and neck cells, MDA1986 (Myers, et al. (2002) *Clin. Cancer Res.* 8:293) and JMAR (Swan, et al. (2003) *Oral Oncol.* 39:648-55); and melanoma cells lines B16F10 (ATCC, Manassas, Va.) and SKMEL28 (CLS, Eppelheim, Germany) were cultured in DMEM medium supplemented with 10% heat-inactivated fetal bovine serum (Sigma-Aldrich, St. Louis, Mo.), 1×MEM-essential amino acid, 1×MEM vitamin, and penicillin/streptomycin (Sigma-Aldrich, St. Louis, Mo.) in a humid environment of 5% $CO_2$ at 37° C. Activity of withanolides against DRO81-1 and TT medullary thyroid cancer cells was also determined.

Cells were cultured in 96 well plates at a concentration of $1$-$2 \times 10^4$ cells/mL. Cell viability was assessed with the non-radioactive cell proliferation MTS assay using Cell Titer 96AQUEOUS One Solution Reagent (PROMEGA, Madison, Wis.), according to the manufacturer's instruction. After a 72-hour treatment, 20 µL of Cell Titer 96AQUEOUS One Solution Reagent were added to each well and incubated for 3 hours at 37° C. 5% $CO_2$, and formazan absorbance was measured at 490 nm. The results of this analysis are presented in Table 1.

TABLE 1

| | $IC_{50}$ (µM) | | | |
|---|---|---|---|---|
| Cell | Withaferin A | X001 | X002 | X003 |
| B16F10 | 0.26 | 0.92 | 0.098 | 0.067 |
| SKMEL28 | 3.96 | 5.06 | 0.81 | 0.54 |
| MDA1986 | 0.8 | 3.34 | 2.24 | 0.91 |
| JMAR | 2.0 | 5.32 | 0.14 | 0.16 |
| NCI-H727 | 3.88 | 1.68 | 0.37 | 0.32 |
| MRC-5 | 0.2 | 12.7 | 0.41 | 0.58 |
| DRO81-1 | 1.09 | 2.29 | 0.48 | 0.34 |
| TT | 1.13 | 1.91 | n.d. | n.d. | n.d., not determined.

X001 exhibited $IC_{50}$ values similar to withaferin A in melanoma and HNSCC, and was more effective against the carcinoid cells than withaferin A.

To determine potency, $IC_{90}$'s were also determined (Table 2).

TABLE 2

| | $IC_{90}$ (µM) | | |
|---|---|---|---|
| Cell | Withaferin A | X001 | X003 |
| B16F10 | 1.23 | 2.64 | 0.33 |
| SKMEL28 | 0.68 | 2.14 | 0.36 |
| JMAR | 3.60 | 4.90 | 1.30 |

The activity of X001, X002 and X003 was further compared to other known compounds (Table 3). A cell viability MTS assay was carried out to determine the anti-cancer effect of the withanolides on human melanoma SKMEL28 cells. Cells were treated for 72 hours and cell viability was determined according to the manufacturer's instruction.

TABLE 3

| Compound | $IC_{50}$ (µM) |
|---|---|
| Withaferin A | 3.15 |
| Viscosalactone B[1] | 18.9 |
| O003 | 3.07 |
| O004 | 14.2 |
| O005 | 11.8 |
| O006 | 8.82 |
| O007 | NA |
| O008 | NA |
| O009 | NA |
| O010 | 17.0 |
| (22R-5β-formyl-6β,27-dihydroxyl-1-oxo-4-norwith-24-enolide)[1] | |
| O011 | NA |
| O015 | NA |

TABLE 3-continued

| Compound | IC$_{50}$ (µM) |
| --- | --- |
| O016 | 648 |
| J027 | 46.1 |
| X001 | 4.71 |
| X002 | 1.25 |
| X003 | 0.221 |
| 17 AAG (17-allylamino-17-demethoxygeldanamycin) | 0.230 |

NA, no activity.
[1]WO 2010/053655

The ability of X001 to induce apoptosis in DRO81-1 and UMSCC-2 HNSCC cells was also assessed by Annexin V/PI staining and flow cytometry. This analysis indicated that after a 24-hour exposure, apoptosis was induced in DRO81-1 cells with a 5 µM concentration of X001 and reached 65% of cells gated toward late apoptosis with a 10 µM concentration of X001. Apoptosis with X001 was confirmed in DRO81-1 medullary thyroid cancer cells with cleavage of PARP starting at 500 nM X001, a level which is below the IC$_{50}$ level of this compound. This result indicates that the compound can induce apoptosis at nanomolar concentrations in this cancer.

As with DRO81-1 cells, 5 µM X001 induced 18% of HNSCC cells to undergo apoptosis (early and late) after a 24-hour exposure. In similar analysis with X003, 50% of UMSCC-2 HNSCC cells underwent apoptosis (early and late) at 1 µM, while 90% of cells underwent apoptosis at 3 µM. Apoptosis with 1 µM X003 was confirmed with PARP cleavage and caspase 3 activation in NCI-H727 cells. Given the structural similarity of X001 and X003, this high level of apoptosis was an unexpected finding.

Several mechanistic pathways were evaluated with X001 following 24 hours treatment at concentrations of 0.5, 1, 3, and 6 µM X001. Both total protein and phosphorylated protein levels of RET, mTOR, P706S kinase were down-regulated in a dose-dependent manner while pERK levels increased at higher concentrations as a compensatory response to apoptosis. These pathways are important carcinogenic and pro-survival pathways in medullary thyroid cancer indicating that X001 is of use as a cytotoxic therapeutic agent in the treatment of medullary thyroid cancer.

EXAMPLE 3

Anticancer Activity of Novel Withanolides

In addition to X002 and X003, additional analogs of X001 were generated. These analogs and their respective designations are shown in Table 4. When evaluated in cell proliferation assays, these compounds also exhibited anti-proliferative activity (Table 5).

TABLE 4

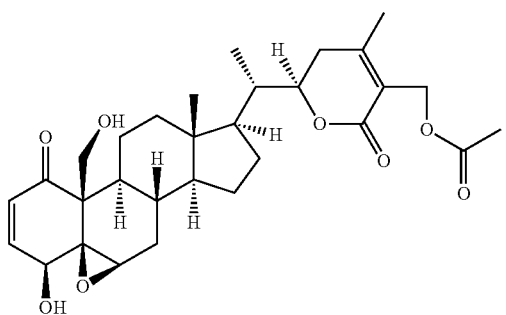

HFM-JA336A

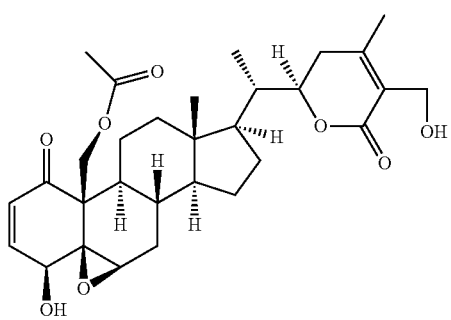

HFM-JA-336B

TABLE 4-continued
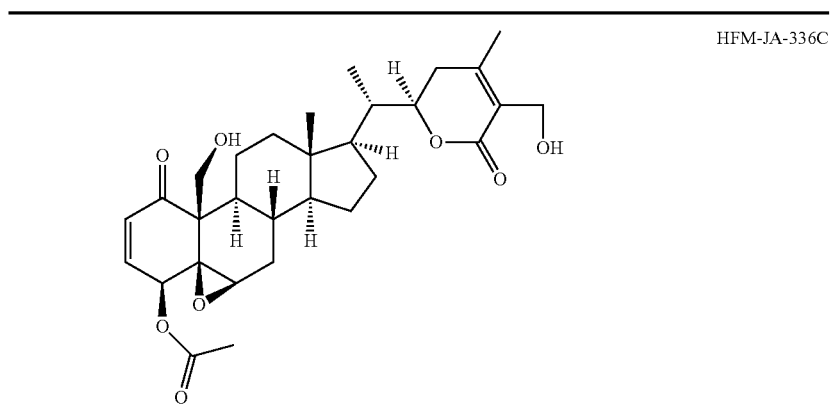
HFM-JA-336C
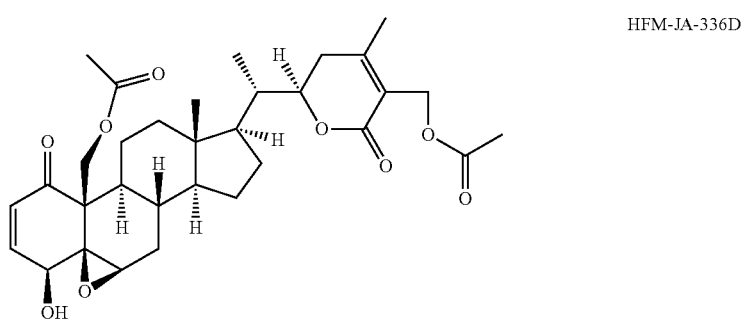
HFM-JA-336D
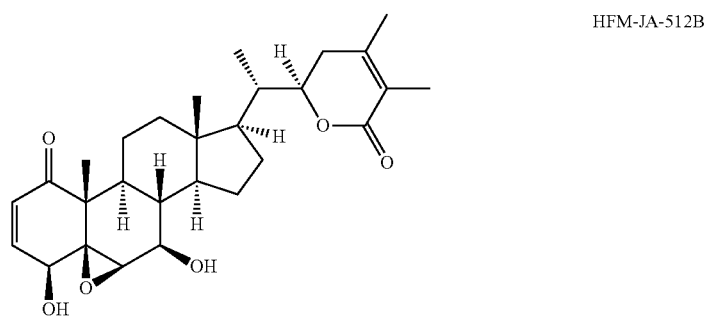
HFM-JA-512B
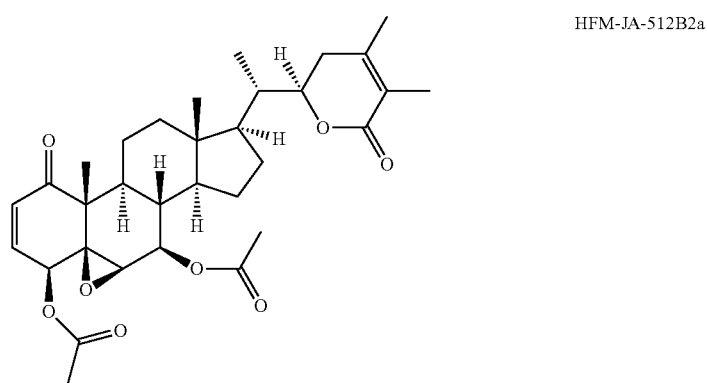
HFM-JA-512B2a TABLE 4-continued
HFM-JA-398B
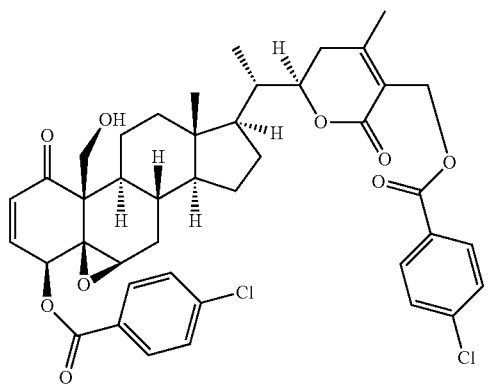
HFM-JA-398E
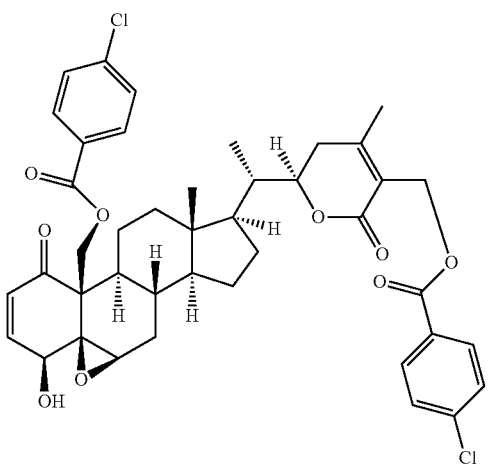
HFM-JA-398H
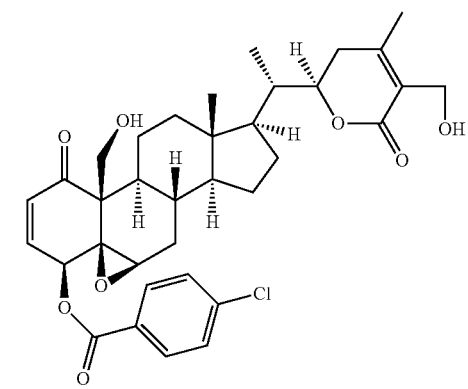
HFM-JA-400
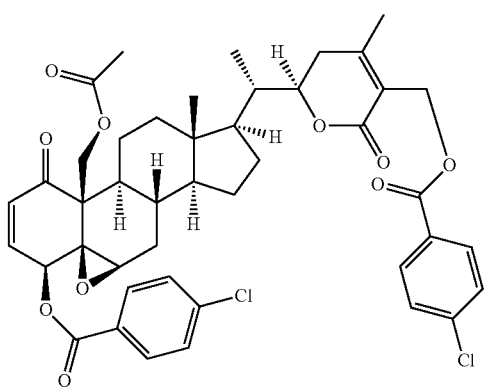

TABLE 4-continued
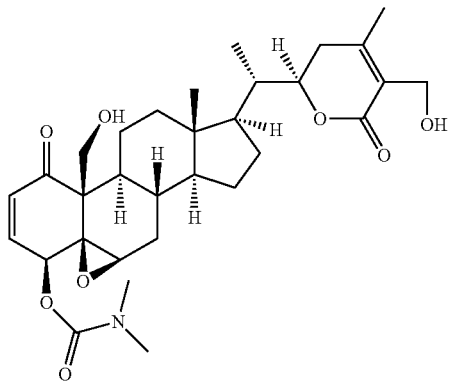
HFM-JA-403
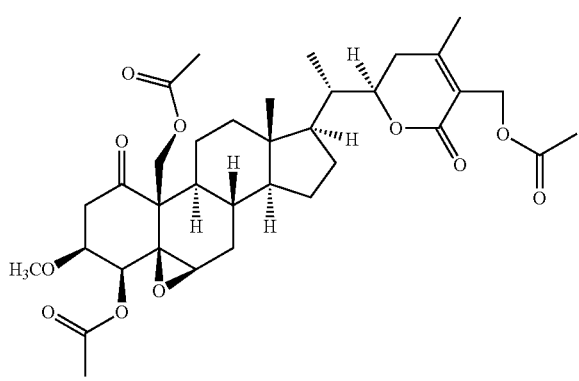
X003B
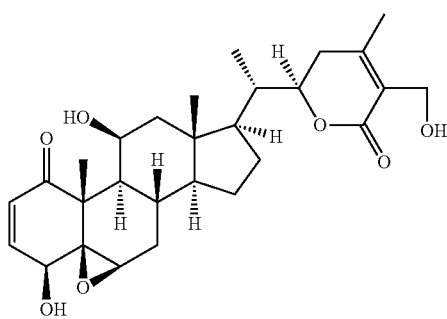
X004
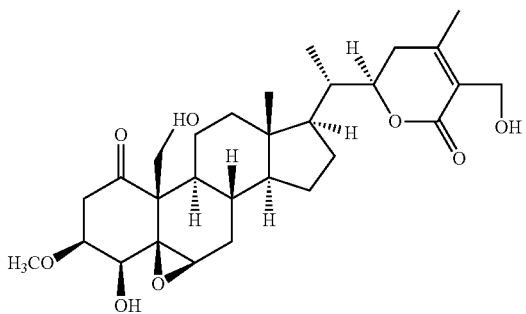
X005

TABLE 4-continued
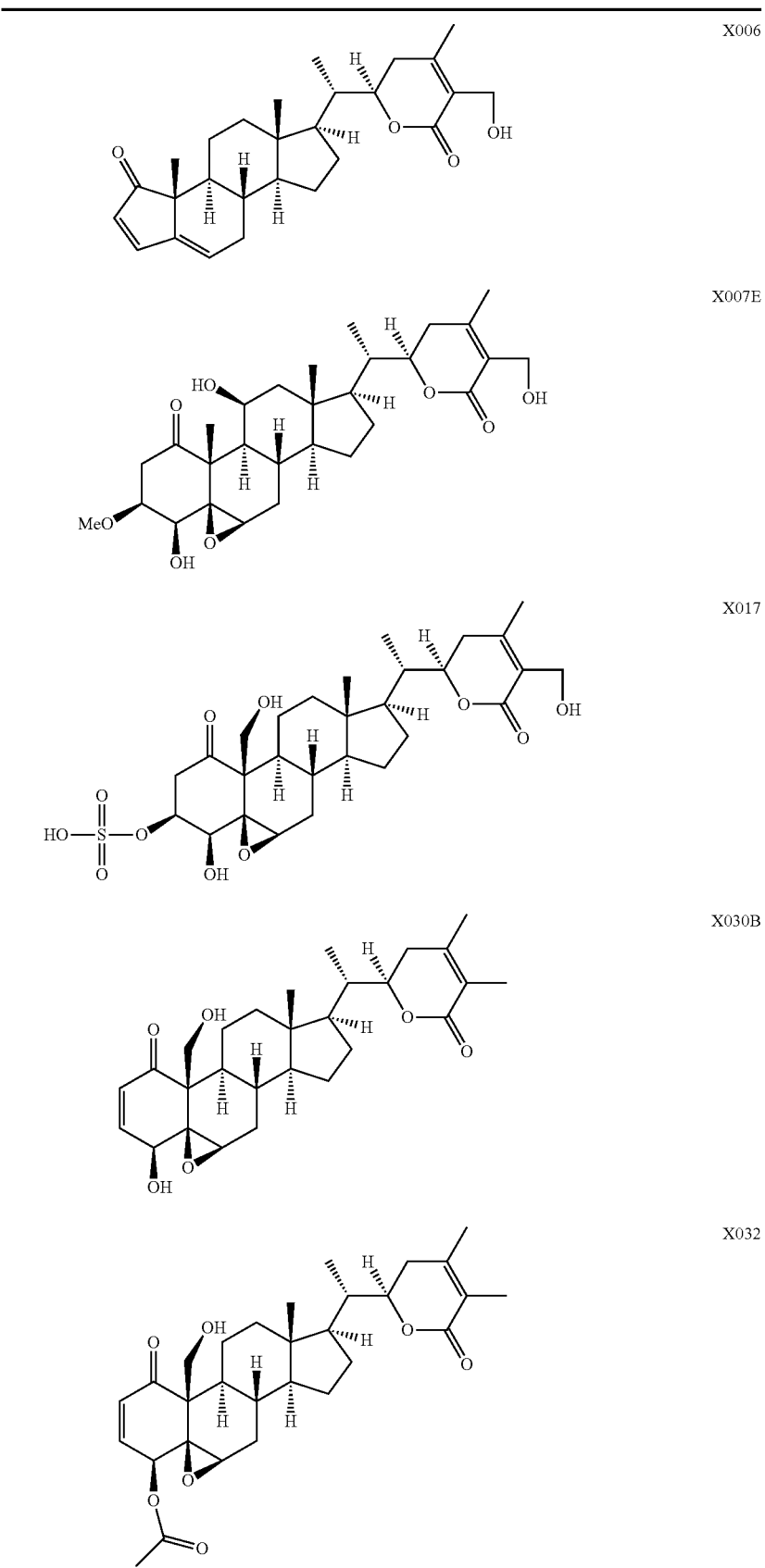
X006
X007E
X017
X030B
X032

TABLE 4-continued
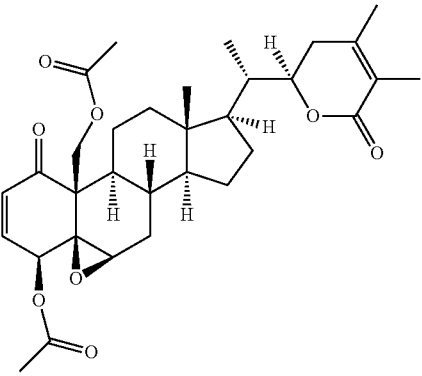
X033
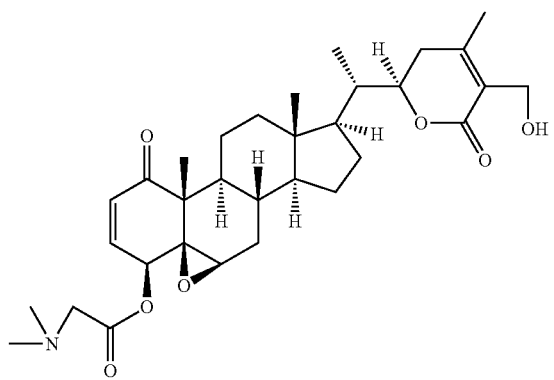
X036
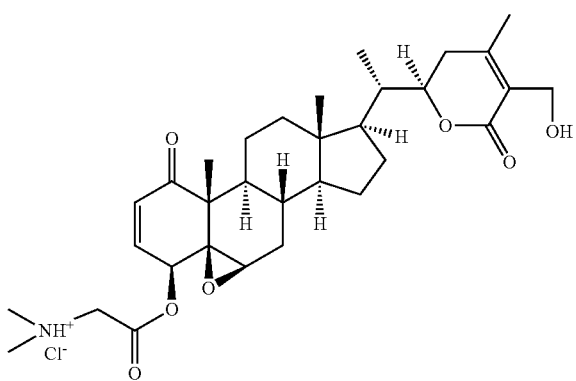
X037A
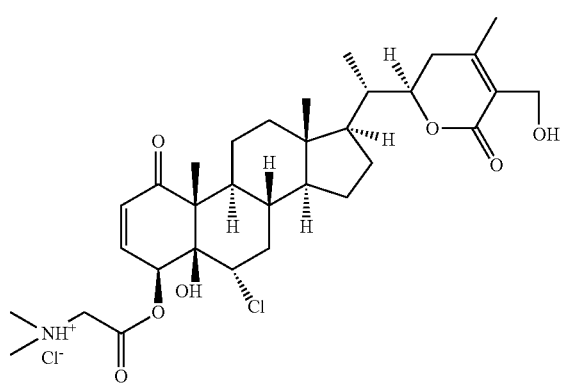
X037B TABLE 4-continued
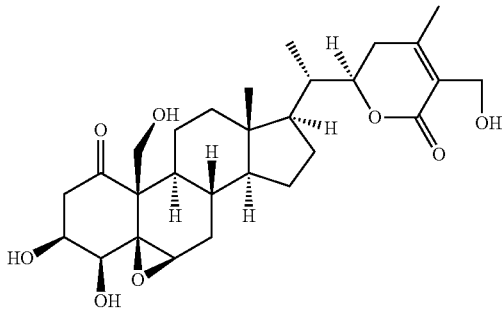
X038
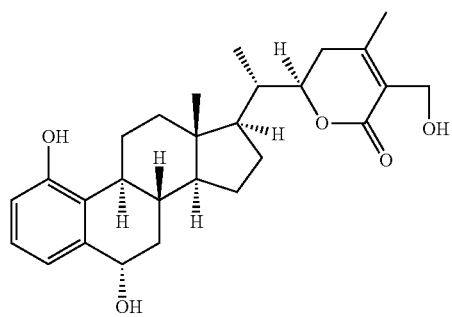
X039
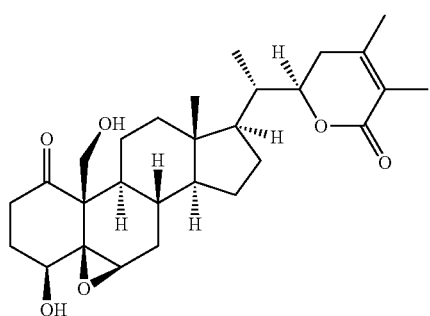
X040
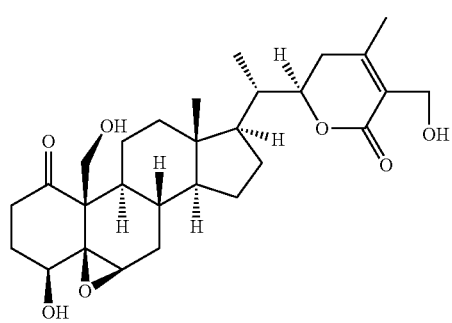
X042
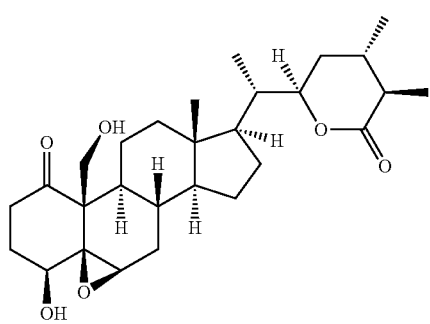
X043

TABLE 4-continued
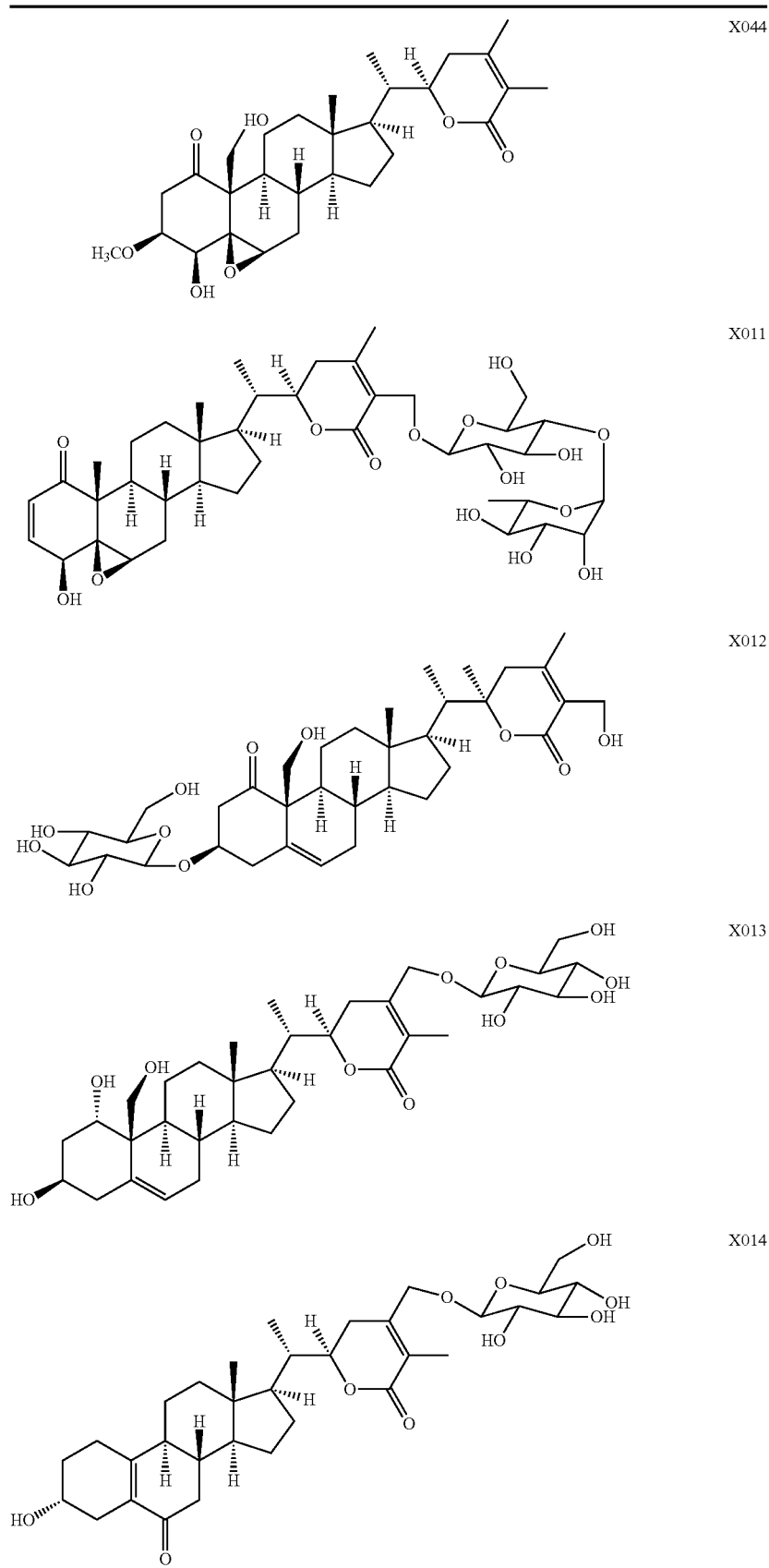

TABLE 4-continued

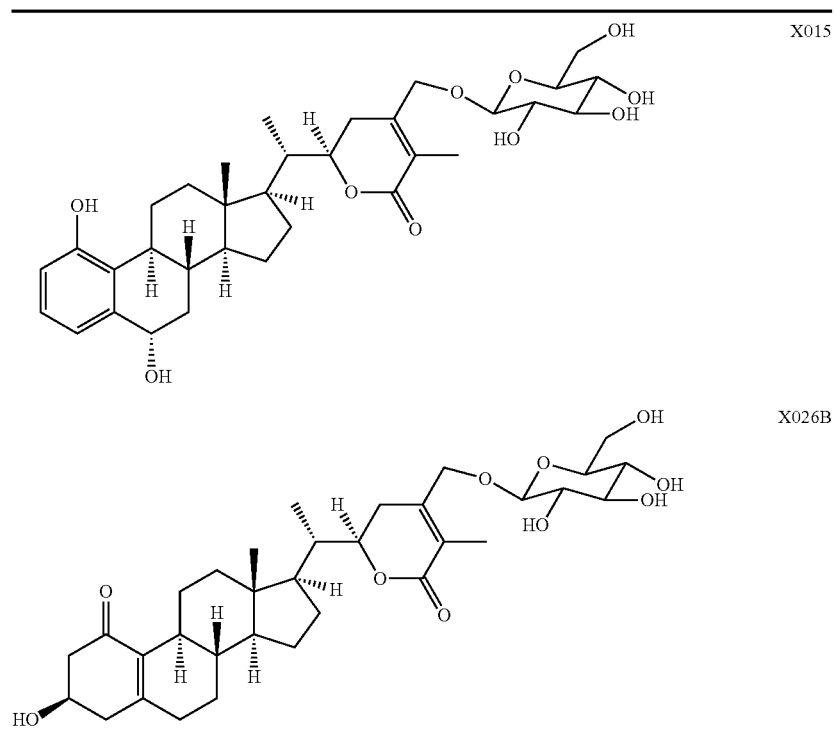

TABLE 5

| Compound | IC$_{50}$ (μM) | | | | |
|---|---|---|---|---|---|
| | B16F10 | SKMEL28 | MDA1986 | JMAR | MRC-5 |
| X004 | 0.49 | 2.99 | 2.64 | 0.77 | 3.60 |
| X005 | 3.21 | 9.27 | >25 | 4.69 | 6.50 |
| X006 | 19.2 | >25 | >25 | 19.7 | >25 |
| X007 | 5.57 | 11.6 | 8.34 | 12 | 7.33 |
| X011 | >25 | 17.40 | 8.10 | 8.24 | 8.72 |
| X012 | 10.7 | >25 | >25 | >25 | >25 |
| X013 | >25 | >25 | >25 | >25 | >25 |
| X014 | >25 | >25 | >25 | >25 | >25 |
| X015 | >25 | >25 | >25 | >25 | >25 |
| X017 | 1.33 | 4.8 | 2.02 | 2.25 | 3.33 |
| X026B | 11.0 | >25 | >25 | >25 | 13.5 |
| X030B | 0.20 | 3.91 | 1.3 | 0.17 | 0.40 |
| X032 | 0.19 | 0.64 | 0.49 | 0.12 | 0.16 |
| X033 | 0.13 | 0.27 | 0.11 | 0.24 | 0.51 |
| X036 | 4.37 | 2.35 | 1.59 | 3.53 | 3.69 |
| X037 | 1.62 | 4.7 | 2.22 | 2.39 | 4.98 |
| HFM-JA-336A | 0.28 | 0.58 | NA | 3.60 | NA |
| HFM-JA-336B | 0.37 | 0.24 | NA | 1.2 | NA |
| HFM-JA-336C | 0.69 | 0.57 | NA | 2.0 | NA |
| HFM-JA-336D | 0.37 | 0.27 | NA | 1.45 | NA |
| HFM-JA-341 | 0.15 | 0.11 | 0.52 | 0.19 | NA |
| HFM-JA-398B | 10 | >25 | >25 | 10.6 | 7.13 |
| HFM-JA-398H | 2.35 | 3.45 | 6.05 | 2.61 | 5.29 |
| HFM-JA-400 | 9.04 | >25 | >25 | >25 | 10.8 |
| HFM-JA-403 | 0.28 | 2.31 | 2.48 | 0.55 | 0.69 |

NA, not available.

To determine potency, IC$_{90}$'s were also determined for select compounds (Table 6).

TABLE 6

| Compound | IC$_{90}$ (μM) | | | |
|---|---|---|---|---|
| | B16F10 | SKMEL28 | MDA1986 | JMAR |
| HFM-JA-336A | 2.7 | 0.86 | 2.7 | 9.80 |
| HFM-JA-336B | 1.2 | 1.16 | 1.2 | 3.10 |
| HFM-JA-336C | 2.5 | 1.21 | 2.5 | 6.50 |
| HFM-JA-336D | 2.5 | 0.42 | 2.5 | 7.10 |

Additional analysis of X005, X032 and X033 was carried out in medullary thyroid cancer cells. In this cell line, X005 had an unexpected and opposite effect on prosurvival and carcinogenic pathways of medullary thyroid cancer compared to X001. This analysis indicated that X005 exhibited a dose-dependent increase in RET, mTOR, 4E-BP1, p70S6 kinase and akt levels, which results in enhanced pro-survival pathway activity and increases in cancer cell growth in vitro. When compared to X001, X005 is missing the double bond in the A-ring. Therefore, this analysis indicates the importance of this double bond in the A-ring to anti-cancer activity.

Similar to X001, treatment of medullary thyroid cancer cells for, 24 hours with X032 or X033 (0.25, 0.5, 1 or 3 μM) resulted in the dose-dependent down-regulation of total protein and phosphorylated protein levels of RET, mTOR, 4E-BP1, P70S6 kinase, while pERK was increased at higher concentrations as a compensatory response to apoptosis. Of note, both X032 and X033 were more potent than X001 in this analysis.

EXAMPLE 4

Induction of Heat Shock Response

Withaferin A induces a heat shock response in cells, possibly as a consequence of F-actin aggregation (WO 2010/

030395). Exposing a heat shock reporter cell line to serial concentrations of the compounds of the invention will demonstrate that the instant compounds can increase heat shock protein expression stimulated. Assays can be carried out by exposing immortalized mouse embryo fibroblasts derived from homozygous Hsf1 knockout mice or their wild-type littermates to compounds of the invention or the known heat shock-inducing Hsp90 inhibitor geldanamycin. Whole cell lysates are prepared in non-ionic detergent buffer and immunoblotted for relative levels of Hsp72, a highly inducible member of the Hsp70 family of molecular chaperones, using a monoclonal antibody. Reactivity is detected using peroxidase-conjugated secondary antibody and chemiluminescent detection. To evaluate the relative ability of compounds to induce a heat shock response at the transcriptional level, a reporter cell line is used (Turbyville, et al. (2006) *J. Nat. Prod.* 69:178-184). These cells are stably transduced with a plasmid encoding enhanced green fluorescent protein (EGFP) under the control of a minimal heat shock response element derived from the promoter region of the Hsp70B gene. They demonstrate a robust, concentration-dependent fluorescent response to known heat shock-modulating drugs such as Hsp90 inhibitors and can be used as a sensitive and specific system to non-destructively monitor induction of the heat shock response in live cells.

EXAMPLE 5

Assessment of Withanolides in Neuroprotection Models

The withanolides of the instant invention can be assessed in one or more known cell-based assay. Alternatively, neuroprotective effects of withanolide(s) can be assessed in one or more in vivo animal models, e.g., in rodents such as mice or rats. One such model is an ischemic stroke model, e.g., a model involving occlusion of the middle cerebral artery (MCAO), optionally followed by reperfusion, e.g., as described by Arboleda-Velasquez, et al. (2008) *Proc. Natl. Acad. Sci. USA* 105(12):4856-4861; Huang, et al. (1994) *Science* 265:1883-1885; or Huang, et al. (1997) *J. Cereb. Blood Flow Metab.* 17:1143-1151. Another model is a spinal cord injury model. See, e.g., Basso, et al. (1995) *J. Neurotrauma* 12(1):1-21; Basso, et al. (1996) *Exp. Neurol.* 139(2):244-256.

EXAMPLE 6

Toxicity Profiles of X001

The in vitro metabolism of X001, as compared to known reference compounds, was analyzed using liver microsomes from human, dog (Beagle), rat (Sprague-Dawley) and mouse (CD-1). The results of this analysis are presented in Table 7.

TABLE 7

| Compound | Mean % Parent Compound Remaining | | | |
| --- | --- | --- | --- | --- |
|  | Human | Dog | Rat | Mouse |
| X001 | 27 | 28 | 31 | 29 |
| Imipramine | 62 | 1 | 0 | 5 |
| Propranolol | 66 | 48 | 0 | 21 |
| Terfenadine | 9 | 84 | 15 | 19 |
| Verapamil | 12 | 31 | 31 | 7 |

Compounds were tested at 1.0E-06 M. Results are from two independent tests.

Cytotoxicity of X001 was analyzed using *Salmonella typhimurium* tester strains TA98, TA100, and TA1535 without S9. The results of this analysis are presented in Table 8.

TABLE 8

| X001 Test | Cytotoxicity (% of Control) | | |
| --- | --- | --- | --- |
| Concentration (M) | TA98 | TA100 | TA1535 |
| 6.3E-07 | 95 | 99 | 99 |
| 1.3E-06 | 89 | 96 | 99 |
| 2.5E-06 | 87 | 101 | 97 |
| 5.0E-06 | 86 | 103 | 98 |
| 1.0E-05 | 86 | 101 | 97 |
| 2.5E-05 | 86 | 93 | 100 |
| 5.0E-05 | 85 | 101 | 109 |
| 1.0E-04 | 98 | 107 | 111 |

Results are the mean of three independent tests.

For comparison, the $IC_{50}$ values of mitomycin C are 4.1-08 M, 3.2E-08, and 6.6E-08 for strains TA98, TA100 and TA1535, respectively.

Additional analysis compared the toxicity of X001 against Ames test strains TA98, TA100, and TA1535 with (+) or without (−) S9, compared to known reference compounds. The results of this analysis are presented in Table 9.

TABLE 9

| | | Positive Significance (− to +++) | | | | | |
| --- | --- | --- | --- | --- | --- | --- | --- |
| | Test | TA98 | | TA100 | | TA1535 | |
| Compound | Conc. (M) | −S9 | +S9 | −S9 | +S9 | −S9 | +S9 |
| X001 | 5.0E-06 | − | − | − | − | − | − |
| | 1.0E-05 | − | − | − | − | − | − |
| | 5.0E-05 | − | − | − | − | − | − |
| | 1.0E-04 | − | − | − | − | − | − |
| Aminoanthracene | 1.0E-05 | − | +++ | − | +++ | − | +++ |
| Mitomycin C | 1.5E-07 | − | − | − | − | − | − |
| Quercetin | 3.0E-05 | +++ | +++ | − | − | − | − |
| Streptoxotocin | 2.5E-06 | − | − | +++ | +++ | +++ | ++ |

Weak positive, if p < 0.05, denoted as "+".
Strong positive, if p < 0.01, denoted as "++".
Very strong positive, if p < 0.001, denoted as "+++".
Negative result denoted as "−".

To determine cardiac toxicity, an hERG channel assay was conducted using a conventional automated patch clamp technique. The results of this analysis for X001 are presented in Table 10.

TABLE 10

| X001 Test Concentration (M) | Mean % Inhibition of Tail Current |
| --- | --- |
| 1.0E-08 | 3.2 |
| 1.0E-07 | 8.4 |
| 1.0E-06 | 9.7 |
| 1.0E-05 | 19.6 |
| 1.0E-04 | 94.4 |

Results are the mean of two independent tests.

Compared to the known hERG-type potassium channel blocker, E-4031, having an $IC_{50}$ value of 1.2E-08, X001 was found to have an $IC_{50}$ value of 2.2E-05.

EXAMPLE 7

Synergistic Activity of X001 and X003 with Imatinib in Inhibiting the Proliferation of Philadelphia-Chromosome Positive Acute Lymphoblastic Leukemia Cells BCR-ABL (Breakpoint Cluster Region-c-abl oncogene 1, non-receptor tyrosine kinase) plays a key role in the pathogenesis of chronic myeloid leukemia (CML) and 30% of acute lymphoblastic leukemia (ALL). Imatinib mesylate is a tyrosine kinase inhibitor (TKI) specific for the abl tyrosine kinase. While imatinib results in high remission rates, Philidelphia-chromosome positive (Ph+) ALL responds poorly compared with CML, and relapse is common. Second generation TKIs have been shown to overcome certain mutations, however, others such as T315I render resistance to all available TKIs. Therefore, there is a critical need for novel pharmacologic therapies for Ph+ ALL.

Heat Shock Protein 90 (HSP90) is a molecular chaperone that facilitates folding and promotes stability of client proteins, including BCR-ABL, and its expression is increased in leukemic cells. HSP90 inhibitors have been shown, in solid tumors as well as in CML, to be effective at inducing apoptosis and inhibiting growth of cells in vitro and tumor growth in vivo. Withanolides, including the steroidal-lactone Withaferin A (WA), have been shown to down-regulate HSP90 activity. Therefore, it was determined whether the X001 and X003 would inhibit Ph+ ALL cell proliferation through down-regulation of BCR-ABL activity.

Cell proliferation was analyzed using MTS assay and Trypan Blue exclusion. Annexin V-FITC/Propidium Iodide flow cytometry was used to analyze the induction of apoptosis in SUP-B15 cells after treatment with anolides. Cell cycle analysis was performed using propidium iodide flow cytometry. Modulation of BCR-ABL and downstream effector proteins was determined by western blot analysis. Syngery between withanolides and TKIs was evaluated using MTS viability to calculate combination indices. Apoptotic synergy was evaluated using Annexin V/PI.

All Solanaceae-derived withanolides tested had $IC_{50}$ values in the nanomolar range in SUP-B15 cells, and in the micromolar range in normal MRC-5 fibroblasts, indicating a large therapeutic index (Table 11).

TABLE 11

| Compound | $IC_{50}$ Value (nM) | | Fold Difference |
|---|---|---|---|
| | SUP-B15 | MRC-5 | |
| Imatinib | 208 | 15,300 | 73X |
| Withaferin A | 132 | 2,200 | 17X |
| X001 | 350 | 8,200 | 23X |
| X003 | 48 | 1,500 | 31X |

To further assess the effects of these withanolides on proliferation and viability of SUP-B15 cells, trypan blue exclusion assay data was collected at both 24 and 72 hour time points, at concentrations of 5×, 2×, 1×, and 0.5×$IC_{50}$ values for each drug, as well as an untreated control. All three withanolides caused significantly decreased viability between 1×-2×$IC_{50}$ values at 72 hours in SUP-B15 cells. X003 was the only drug to cause significant cell death at 24 hours at $IC_{50}$ values, with no further decrease in viability seen at 72 hours, indicating that it kills much faster than X001 or Withaferin A. Withaferin A did not cause significant cell death at 24 hours at any concentration tested, while X001 caused death at 24 hours with 2× and 5×$IC_{50}$ values. All three drugs did result in approximately the same decrease in viability at 72 hours.

Induction of apoptosis by withanolides Withaferin A, X001, and X003 in SUP-B15 cells was obtained using Annexin V/propidium iodide staining after 48 hour treatments with varying concentrations of drug, and analyzed using flow cytometry. Results indicate that at high concentrations (approximately 10×$IC_{50}$ values for Withaferin A and X001, and 4×$IC_{50}$ values for X003) almost all cells were in either late or early apoptosis. At no concentrations was the population of cells in necrosis significant. While early apoptosis was not evident after 48 hour treatment with either X001 or X003, it is likely given the trypan blue exclusion results that these cells enter early apoptosis at an earlier time point.

Cell cycle modulation was examined using PI staining after 48 hour treatment with anolides Withaferin A and X001 and subsequent flow cytometry. An increase in the number of cells was observed in G2/M arrest in a concentration dependent manner initially, followed by a decrease in the population of cells in G2/M at higher (~10×$IC_{50}$) concentrations (Table 12). This may indicate that at lower concentrations, this cell cycle arrest plays a more prominent role in the mechanism of action while other events (such as induction of apoptosis) play a more crucial role at higher concentrations or longer time points.

TABLE 12

| Compound | Conc. (nM) | Cell Cycle (%) | | |
|---|---|---|---|---|
| | | G0/G1 | S | G2/M |
| WA | 0 | 51.1 | 22.3 | 26.6 |
| | 80 | 49.9 | 22.2 | 27.8 |
| | 160 | 50.2 | 21.4 | 28.4 |
| | 320 | 38.4 | 14.8 | 46.8 |
| | 640 | 23.7 | 5.3 | 71 |
| | 1280 | 47.1 | 18.6 | 34.3 |
| X001 | 0 | 51 | 20.4 | 28.6 |
| | 200 | 53.1 | 19.5 | 26.4 |
| | 400 | 54.6 | 18.3 | 27.1 |
| | 800 | 47.5 | 10.3 | 42.2 |
| | 1600 | 39.9 | 15.7 | 44.5 |
| | 3200 | 49.9 | 18.6 | 31.5 |
| X003 | 0 | 51.7 | 24.4 | 23.9 |
| | 15 | 57.4 | 21.9 | 20.7 |
| | 30 | 66.4 | 9.5 | 24 |
| | 60 | 62.5 | 15.3 | 22.2 |
| | 120 | 52.6 | 17.4 | 30 |

With a 24-hour treatment of Ph+ALL cells with anolides at $IC_{50}$ concentrations, western blot analysis demonstrated >50% down-regulation of phospho-BCR-ABL protein levels and confirmed apoptosis with caspase-3 activation and PARP cleavage. Moreover, levels of Akt, Stat5, HSP90 and HSP70 were decreased and levels of p53 were increased.

Analysis of the combination of withanolides Withaferin A, X001, and X003 each with imatinib was studied using MTS assays to determine the viability of SUP-B15 Ph+ALL cells in various dosing combinations. Concentrations of 0.25×, 0.5×, 0.75×, and 1×$IC_{50}$ values of each withanolide were combined with imatinib at the same concentrations (0.25×, 0.5×, 0.75×, and 1×$IC_{50}$) for a total of 16 different combinations, representing every combination possible of those four concentrations. Percentage viability was analyzed to determine combination index (CI) and plotted on an isobologram, which shows whether the drug combination was synergistic (below the line; a CI<1), additive (on the line; a CI=1), or antagonistic (above the line; a CI>1). Withaferin A in combination with imatinib only showed synergy at three of the concentrations tested and had a combination index (CI) of 1.3, while X001 and X003 showed synergy at all concentrations tested and had CIs of 0.511 and 0.136, respectively.

Therefore, X001 and X003 demonstrate potent anti-leukemic effects against Ph+ ALL cells in vitro through down-regulation of BCR-ABL activity with resulting induction of apoptosis and cell-cycle shift. These compounds exhibit excellent synergy with imatinib and would be of use in the treatment of patients with Ph+ ALL.

EXAMPLE 8

Sensitivity of Breast Cancer Cells to X001

The activity of X001 against various breast cancer cell lines was analyzed. Cell proliferation was analyzed using MTS assay. This analysis (Table 13) indicated that breast cancer cell lines were more sensitive to X001 than normal cell lines but high concentrations of X001 could kill the normal cells as well.

TABLE 13

| Cell Line | Log ECF |
|---|---|
| MDA-MB-231 | 1.25 |
| MDA-MB-468 | 0.32 |
| HCC1937 | 0.71 |
| BT20 | 0.91 |
| MCF-7 | 1.88 |
| MRC5 | 4.59 |
| HMLEC | 2.54 |

Among the various breast cancer cell lines, triple-negative MDA-MB-468 and BT20 cells and HCC1937 (BRCA-1 mutant) cells were the most sensitive to X001 in the MTS assay. To further analyze the observed inhibition, the activity of X001 against MDA-MB-231, BT20 and HCC1937 cells was analyzed in a clonogenic assay, wherein cells were treated for 24 hours with X001 and cultured for two weeks. This analysis indicated that X001 strongly inhibited MDA-MB-231 and HCC1937 colony formation at 1-2 µM, wherein inhibition of BT20 colony formation was not as potent at the 1-2 µM concentration.

After a 24-hour treatment with X001, cell cycle analysis indicated that X001 caused G2/M arrest of MDA-MB-231 cells at 4 and 8 µM, G2/M arrest of BT20 cells at 2 µM and G2/M cell cycle arrest in ER+ MCF-7 cells at 1-2 µM.

The ability of X001 to induce apoptosis in breast cancer cells was assessed by Annexin V-FITC/Propidium Iodide flow cytometry. This analysis indicated that at least 4 µM of X001 is needed to induce apoptosis in MDA-MB-231 cells. Therefore, this cell line was not very sensitive to X001 in this assay. Furthermore, 1-4 µM X001 did not induce apoptosis in MCF-7 cells at 24 and 48 hours, although some cells began to float with 8 µM X001. In contrast, BT20 cells were more sensitive to X001 than MDA-MB-231 cells in terms of apoptosis, however, MDA-MB-231 cells were more sensitive to X001 than BT20 when using clonogenic assay.

With a 24-hour or 48-hour treatment of MDA-MB-231 cells with X001 at 1, 2, 4, or 8 µM, western blot analysis demonstrated caspase-3 activation at 4-8 µM and PARP cleavage. Moreover, levels of BRCA-1, HSF1, mutant p53, Notch1 and Jagged1 were decreased; however, the Akt pathway was not modulated by X001.

These data indicate that, like Withaferin A (WA), X001 induces G2/M phase cell cycle arrest in various breast cancer cell lines. However, the apoptotic response varies more with X001 in breast cancer cells as compared to with WA. Like WA, X001 down-regulates HSF1, BRCA-1, mutant p53, Notch1 and Jagged1.

EXAMPLE 9

Dose-Dependent Activity of Withanolides in Pancreatic Cancer

The activity of the withanolides of this invention were tested in pancreatic cancer cells. In this analysis, 0.5, 2.0 and 10.0 µM amounts of X001, X002, X003, X004, X007, X017 and X030 were tested against HS766T, Mia PaCa-2 and Panc1 cancer cell lines. Cell viability was determined after 48 hours and it was shown that each compound reduced cell viability by at least 50% at the 2.0 and 10.0 µM amounts, with X002 and X003 being the most effective at any concentration. Moreover, $IC_{50}$ values were determined for these compounds (Table 14).

TABLE 14

| | $IC_{50}$ (µM) | |
|---|---|---|
| Withanolide | HS766T | MIA PaCa2 |
| X001 | 1.3 | 0.8 |
| X002 | 0.4 | 0.22 |
| X003 | 0.4 | 0.35 |
| X004 | 1.6 | 1.3 |
| X017 | 1.8 | 1.4 |
| X030 | 0.8 | 0.8 |

To monitor the activation of heat shock factor (HSF) and heat shock-mediated signal transduction pathways, Hs766T cells were transfected with a HSE-luciferase construct, then treated with 3 mM of the selected withanolides for 8 hours. The cells were heat shocked at 42° C. for 30 minutes and allowed to recover at 37° C. for 8 hours. Cells were lysed and luciferase activity was measured on a plate reader. The results of this analysis indicated that X002, X003 and X030 substantially reduced the increases in luciferase activity observed in control cells. Furthermore, as determined by western blot analysis, treatment of Hs766T and MIA PaCa-2 cells with either X002 or X003 induced oxidative and proteotoxic stress, while depleting hsf1 and client proteins of Hsp90.

Levels of HSF1, Hsp70 and Hsp40 mRNA were also determined in response to treatment with SX002 or X003 for 8 or 16 hours. The results of this analysis are presented in Table 15 and show that X002 and X003 substantially increased the mRNA expression of Hsp70 and Hsp40.

TABLE 15

| | | X002 | | X003 | |
|---|---|---|---|---|---|
| mRNA | Control | 8 hours | 16 hours | 8 hours | 16 hours |
| HSF1 | 1.0 | 1.3 | 1.1 | 1.2 | 1.1 |
| HSP70 | 1.0 | 56.6 | 196.7 | 30.8 | 183.1 |
| HSP40 | 1.0 | 13.1 | 15.3 | 8.3 | 14.2 |

However, pretreatment of Hs766T with X003 failed to block heat shock-induced Hsp70 and Hsp40 protein levels. For this analysis, Hs766T cells were incubated with X003 for 8 hours, followed by a 30-minute heat shock at 42° C. The cells were further incubated for 8 hours and Hsp70 and Hsp40 levels were determined.

To determine whether the instant withanolides could be used in combination with other treatment regimes, Hs766T pancreatic cancer cells were either treated with 0.1, 0.2 or 0.3 μM X003; 10 or 20 nM carfilzomib; or co-treated with carfilzomib (10 nM) and either 0.1, 0.2 or 0.3 μM X003. Based upon the percent of apoptosis, this analysis indicated that co-treatment with carfilzomib enhances X003-induced apoptosis of pancreatic cancer cells.

What is claimed is:

1. A compound having the structure:

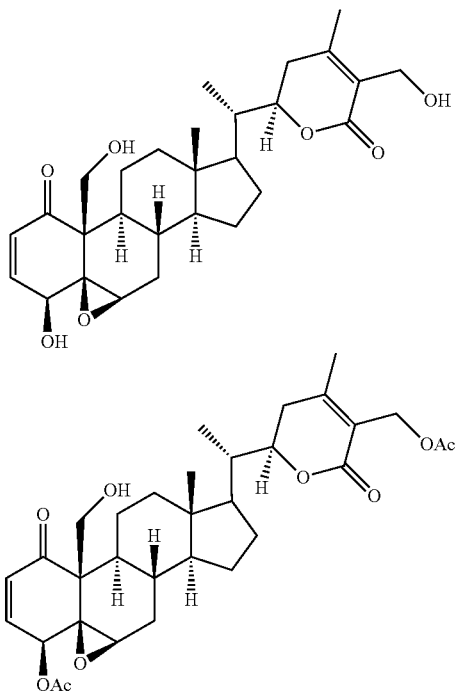

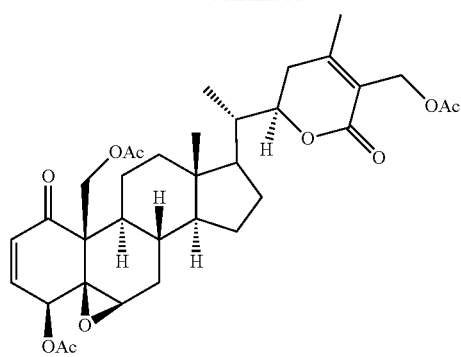

or

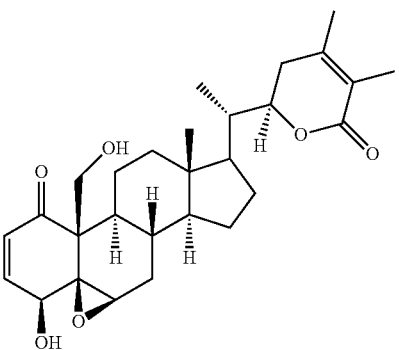

2. A method for treating cancer comprising administering to a subject in need thereof an effective amount of a compound of claim 1, thereby treating the subject's cancer.

3. A pharmaceutical composition comprising a compound of claim 1 and a pharmaceutically acceptable carrier.

* * * * *